US006171522B1

(12) United States Patent
Michot et al.

(10) Patent No.: US 6,171,522 B1
(45) Date of Patent: Jan. 9, 2001

(54) HETEROCYCLIC AROMATIC ANION SALTS, AND THEIR USES AS IONIC CONDUCTING MATERIALS

(75) Inventors: Christophe Michot, Grenoble (FR); Michel Armand, Montreal (CA); Michel Gauthier, La Prairie (CA); Yves Choquette, Sainte-Julie (CA)

(73) Assignees: Hydro-Québec, Quebec (CA); Centre National de la Recherche Scientifique, Paris (FR)

( * ) Notice: Under 35 U.S.C. 154(b), the term of this patent shall be extended for 0 days.

(21) Appl. No.: 09/101,811

(22) PCT Filed: Dec. 30, 1997

(86) PCT No.: PCT/CA97/01011

§ 371 Date: Nov. 19, 1998

§ 102(e) Date: Nov. 19, 1998

(87) PCT Pub. No.: WO98/29396

PCT Pub. Date: Jul. 9, 1998

(30) Foreign Application Priority Data

Dec. 30, 1996 (CA) .................................................. 2194127
Mar. 5, 1997 (CA) .................................................. 2199231

(51) Int. Cl.[7] .............................. H01B 1/12; H01M 6/14; C07D 343/00; G02F 1/15
(52) U.S. Cl. ...................... 252/500; 252/62.2; 429/188; 429/194; 429/199; 549/14; 549/357; 502/102; 502/300; 502/302; 345/49; 359/265
(58) Field of Search ................. 252/500, 62.2; 549/14, 357; 429/188, 194, 199; 502/102, 300, 302; 345/49; 359/265

(56) References Cited

U.S. PATENT DOCUMENTS 5,817,376   10/1998   Everaerts et al. ................. 427/483

Primary Examiner—Mark Kopec
(74) Attorney, Agent, or Firm—Hutchins, Wheeler & Dittmar

(57) ABSTRACT

The invention relates to ionic compounds in which the anionic load has been displaced, and the uses of these compounds. A compound disclosed by the invention comprises an anionic portion combined with at least one cationic portion $M^{+m}$ in sufficient numbers to ensure overall electronic neutrality. The anionic portion is comprised of one of the groups (A) and (B):

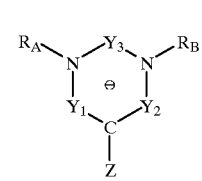

(A)

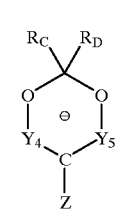

(B)

wherein $Y_1$, $Y_2$, $Y_3$, $Y_4$ and $Y_5$ represent a carbonyl group, a sulfonyl group, a thiocarbonyl group, a thionyl group, a —C(=NCN)— or a —C(=C(CN)$_2$)— group; Z represents an electroattractive radical; each of the substituents, $R_A$, $R_B$, $R_C$ and $R_D$ represents independently of one another a monovalent or divalent organic radical or is part of a polymer chain, with at least one of the substituents $R_C$ and $R_D$ being a perfluorinated radical. The compounds can be used especially for ionic conducting materials, electronic conducting materials, colorants, and the catalysis of various chemical reactions.

81 Claims, 1 Drawing Sheet

HETEROCYCLIC AROMATIC ANION SALTS, AND THEIR USES AS IONIC CONDUCTING MATERIALS

It is an object of the present invention to provide ionic compounds in which the anionic charge is delocalized, and their uses.

Derivatives of non-nucleophilic or slightly basic anions have an increasing importance in all applications of chemistry to stabilize or activate various cationic charges such as those of colouring materials or intermediate species in polymerizations. They also act as intermediates for various reactions of organic chemistry. In electrochemistry, media other than water are more and more relied upon for applications such as primary or secondary generators, supercapacitances, systems of modulation of light. The introduction of a weak ionic conductivity in the usual materials (polymers, combustible liquids), enables to disperse electrostatic charges.

Derivatives which are derived from coordination anions of the type $BF_4^-$, $PF_6^-$, $AsF_6^-$, are mainly known, however, they have a limited stability due to dissociation equilibrium releasing the fluoride ion and the corresponding Lewis acid, both causing parasite reactions and presenting a toxicity which is not negligible. The perchlorate anion $ClO_4^-$ is thermally unstable and dangerous. On the other hand, anions derived from bis(perfluoroalkylsulfonyl)imides which present interesting properties are known. However, this type of chemistry is relatively difficult to control, in particular during the preparation of precursors of the type $R_FSO_2$—.

On the other hand, pyrimidinetrione (barbituric acid) and its derivatives which are obtained by replacing an atom of oxygen by an atom of sulfur (thiobarbituric acid) are known. Also known is the possibility to produce salts with 2,2-dimethyl-1,3-dioxane-4,6-dione ("Meldrum acid"). In both cases, the acids are relatively weak ($pK_A$) of the order of 5 in water, of the order of 10 in dimethylsulfoxide). Their salts are neither easily soluble nor easily dissociable in organic solvents. In the case of pyrimidinetrione, the hydrogen bonds formed by the protons associated with nitrogen reinforce this insolubility. Their substitution with alkyl radicals strongly decreases the strength of the acid.

The inventors have now found that, surprisingly, the solubility and dissociation of the salts obtained from pyridiminandrione derivatives and its homologues by substitution on the carbon atom in position 5, or on the nitrogens in positions 1 and 3 is considerably increased when the substituents have an electronically attracting power. The same is true with respect to compounds derived from 1,3-dioxane-4,6-diones and their homologues which carry a substituent which is an electroattractor on carbon 2 and/or carbon 5. The choice of substituents and the numerous possible combinations in three substitution sites for each family give various materials for which it is possible to modulate the physical or chemical properties to a large extent. These compounds have interesting properties for the above-mentioned applications and their preparation calls for materials which are more readily accessible. For example, it is possible to obtain stable anionic heterocycles incorporating smaller quantities of fluorine, or to use as starting products fluorinated compounds which are easily accessible. Certain compounds may totally prevent having to rely on fluorine atoms.

BRIEF DESCRIPTION OF THE DRAWINGS

The sole FIGURE shows the utilization, U, of a lithium salt expressed as a percentage, versus the number of voltage cycles between 1/8 and 3.3 volts.

DETAILED DESCRIPTION OF PREFERRED EMBODIMENT(S)

Figure 1:
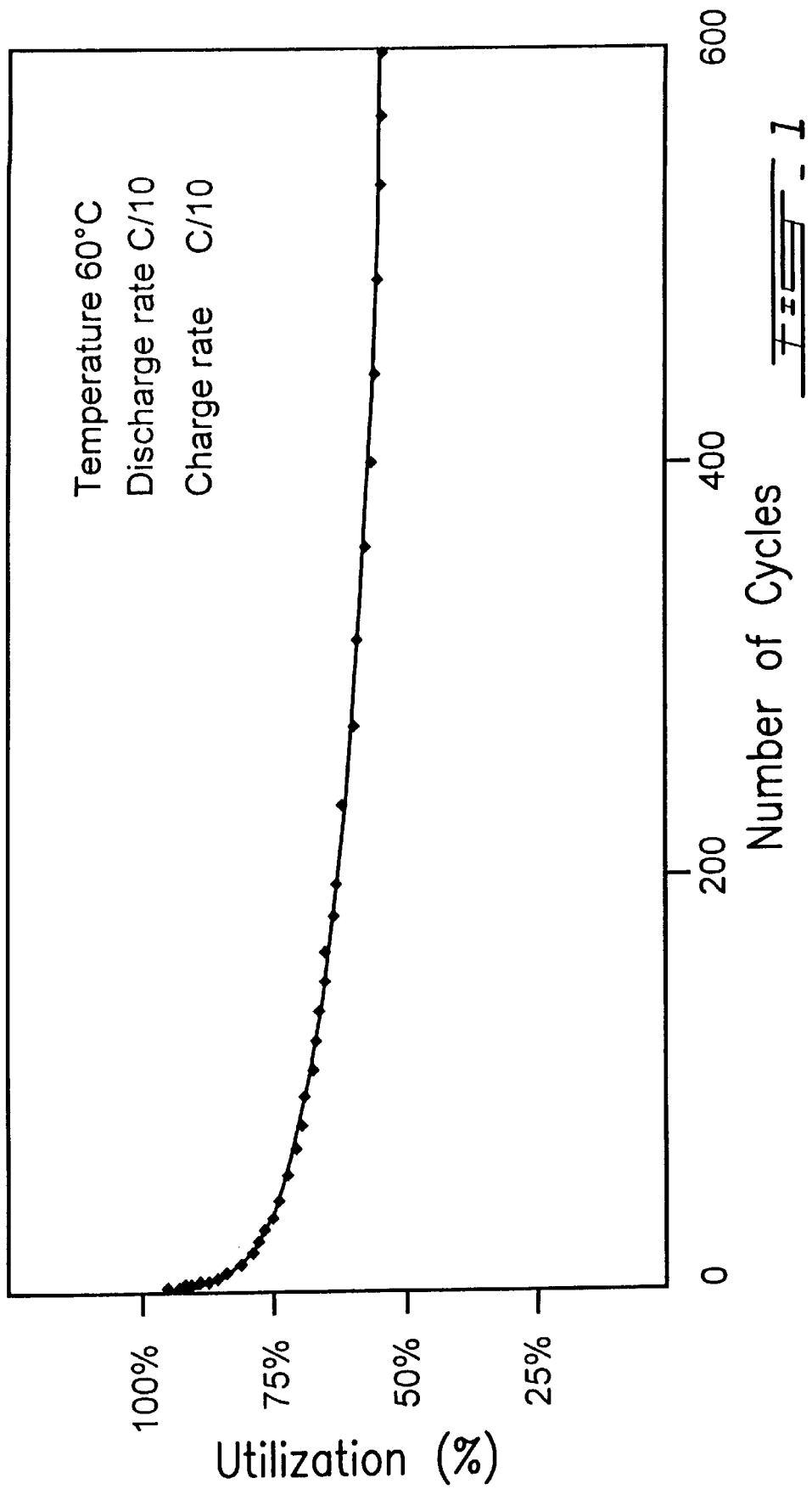

A compound of the present invention comprises at least one anionic part associated to at least one cationic part M in sufficient number to ensure an electronic neutrality of the assembly. It is characterized in that M is an hydroxonium, a nitrosonium $NO^+$, an ammonium —$NH_4^+$, a metallic cation having a valence m, an organic cation having a valence m or an organometallic cation having a valence m, and in that the anionic part is an aromatic heterocycle corresponding to one of the formulae

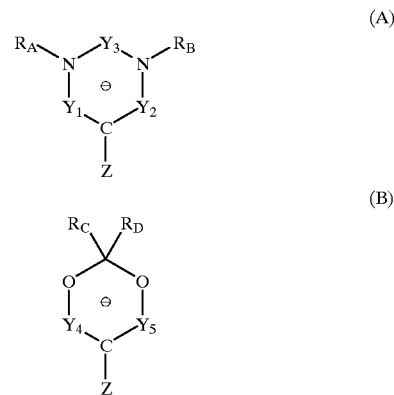

in which:

$Y_1$, $Y_2$, $Y_3$, $Y_4$ and $Y_5$ represent independently from one another a carbonyl group, a sulfonyl group, a thiocarbonyl group, a thionyl group, a —C(=NCN)— group or a —C(=C(CN)$_2$)— group;

Z represents an electroattractor radical having a Hammett parameter at least equal to that of a fluorine atom;

each of the substituents $R_A$, $R_B$, $R_C$ and $R_D$ represents independently from one another a monovalent or trivalent organic radical, or is part of a polymer chain, one at least of the substituents $R_C$ and $R_D$ being a perfluorinated radical. Preferably, the organic radical has 1 to 20 carbon atoms.

In a compound of the present invention, the cation may be a metallic cation selected from alkali metal cations, alkali-earth metal cations, transition metal cations, trivalent metal cations, rare earth cations. By way of example, there may mentioned $Na^+$, $Li^+$, $K^+$, $Sm^{3+}$, $La^{3+}$, $Ho^{3+}$, $Sc^{3+}$, $Al^{3+}$, $Y^{3+}$, $Yb^{3+}$, $Lu^{3+}$, $Eu^{3+}$.

The cation may also be an organometallic cation, for example a metallocenium. By way of example, there may be mentioned cations derived from ferrocene, titanocene, zirconocene, an indenocenium or a metallocenium arene, cations of transition metals complexed with ligands of the phosphine type possibly having a chirality, organometallic cations having one or more alkyl or aryl groups covalently fixed to an atom or a group of atoms, such as methylzinc, phenylmercury, trialkyltin or trialkyllead cations. The organometallic cation may be part of a polymer chain.

According to a variant of the invention, the compounds of the invention have an organic cation selected from the group consisting of $R_3O^+$ (oxonium), $NR_4^+$ (ammonium), $RC(NHR_2)_2^+$ (amidinium), $C(NHR_2)_3^+$ (guanidinium), $C_5R_6N^+$ (pyridinium), $C_3R_5N_2^+$ (imidazolium), $C_3R_7N_2^+$ (imidazolinium), $C_2R_4N_3^+$ (triazolium), $SR_3^+$ (sulfonium), $PR_4^+$ (phosphonium), $IR_2^+$ (iodonium), $(C_6R_5)_3C^+$ (carbonium). In a given cation, the radicals R may all be identical. However, a cation may also include radicals R which are different from one another. A radical R may be an H or it is selected from the following radicals:

alkyl, alkenyl, oxa-alkyl, oxa-alkenyl, aza-alkyl, aza-alkenyl, thia-alkyl, thia-alkenyl, sila-alkyl, sila-alkenyl, aryl, arylalkyl, alkyl-aryl, alkenyl-aryl, dialkylamino and dialkylazo radicals;

cyclic or heterocyclic radicals possibly comprising at least one lateral chain comprising heteroatoms such as nitrogen, oxygen, sulfur;

cyclic or heterocyclic radicals possibly comprising heteroatoms in the aromatic nucleus;

groups comprising a plurality of aromatic or heterocyclic nuclei, condensed or non-condensed, possibly containing at least one hydrogen, oxygen, sulfur or phosphorus atom.

When an onium cation carries at least two radicals R which are different from H, these radicals may together form an aromatic or non-aromatic cycle, possibly enclosing the center carrying the cationic charge.

When the cationic part of a compound of the invention is an onium cation, it may be either in the form of an independent cationic group which is only bound to the anionic part by the ionic bond between the positive charge of the cation and the negative charge of the anionic part. In this case, the cationic part may be part of a recurring unit of a polymer.

An onium cation may also be part of the radical Z carried by the anionic aromatic nucleus. In this case, a compound of the invention constitutes a zwitterion.

When the cation of a compound of the invention is an onium cation, it may be selected so as to introduce in the compound substituents enabling to confer to said compound specific properties. For example, the cation $M^+$ may be a cationic heterocycle with aromatic character, including at least one nitrogen atom which is alkylated in the cycle. By way of example, there may be mentioned an imidazolium, a triazolium, a pyridinium, a 4-dimethylamino-pyridinium, said cations possibly carrying a substituent on the carbon atoms of the cycle. Among these cations, those which give an ionic compound according to the invention in which the melting point is lower than 150° C. are particularly preferred. Such a compound having a low melting temperature is particularly useful for preparing materials with protonic conduction. A particularly preferred material with protonic conduction comprises a compound according to the invention in which the cation is formed by the addition of a proton on the nitrogen or an imidazole or a triazole, as well as the corresponding nitrogenated base in a proportion of 0.5 to 10 in molar ratio.

A compound of the invention in which the cation M is a cationic group having a bond —N=N—, —N=N$^+$, a sulfonium group, an iodonium group, or a substituted or non-substituted arene-ferrocenium, possibly incorporated in a polymeric network, is interesting in as much as it is activatable by a source of actinic energy of appropriate wavelength. Specific examples of such compounds include those in which the cation is a diaryliodonium cation, a dialkylaryliodonium cation, a triarylsulfonium cation, a trialkylaryl sulfonium cation, or a substituted or non-substituted phenacyl-dialkyl sulfonium cation. The above-mentioned cations may be part of a polymer chain.

The cation M of a compounds of the invention may include a group 2,2'[azobis(2-2'-imidazolinio-2-yl) propane]$^{2+}$ or 2,2'-azobis(2-amidiniopropane)$^{2+}$. The compound of the invention is then capable of releasing, under the action of heat or an ionizing radiation, radicals which enable to initiate reactions of polymerization, of cross-linking or, in a general manner, chemical reactions involving free radicals. Moreover, these compounds are easily soluble in polymeric and monomeric organic solvents of the same polarity, contrary to the derivatives of anions of the type Cl$^-$ which are usually associated with these types of compounds. They present, on the other hand, a negligible vapor pressure contrary to the other free radical initiators of the peroxide or azo type, which is a considerable advantage for preparing polymers in thin films, the volatility of the initiator having as a consequence a bad polymerization or cross-linking of the surface of the film.

The choice of substituents enables to adjust the properties of an ionic compound of the invention.

According to an embodiment of the invention, the substituents $R_A$ and $R_B$ on the one hand, one of the substituents $R_C$ and $R_D$ on the other hand, may independently from one another be an alkyl, an alkenyl, an oxa-alkyl, an oxa-alkenyl, an aza-alkyl, an aza-alkenyl, a thia-alkyl, a thia-alkenyl radical, said radicals possibly carrying at least one aryl group.

b) an aryl possibly carrying at least one radical as defined in a);

c) an alicyclic radical or an aromatic radical possibly carrying at least one lateral chain comprising a heteroatom or possibly comprising at least one heteroatom in the cycle;

d) a radical as defined above in a), b) and c) and additionally carrying halogen atoms, in halogenated or perhalogenated form.

Among the above radicals, alkyl radicals and alkenyl radicals having 1 to 10 carbon atoms, halogenated or perhalogenated alkyl or alkenyl radicals having 1 to 10 carbon atoms, and oxa-alkyl or oxa-alkenyl radicals having 1 to 10 carbon atoms are particularly preferred.

The substituent Z may be selected from the group consisting of —F, —Cl, —Br, —CN, —NO$_2$, —SCN and —N$_3$. Z may also be a —C$_n$F$_{2n+1}$, —O—C$_n$F$_{2n+1}$, —S—C$_n$F$_{2n+1}$, —CH$_2$—C$_n$F$_{2n+1}$, OCF=CF$_2$ or —SCF=CF$_2$ radical, $1 \leq n \leq 8$. In addition, Z may be a radical which comprises a heterocycle derived from pyridine, pyrazine, pyrimidine, oxadiazole or thiadiazole, which is fluorinated or non-fluorinated.

According to another embodiment, Z is a radical $R_E Y_E$— or a radical $R_E R_G PO$— in which $Y_E$ represents a carbonyl group, a sulfonyl group, or a thionyl group, and $R_E$ and $R_G$ represent independently from one another a halogen or an organic radical. The substituents comprising a sulfonyl group are particularly preferred. Each of the substituents $R_E$ and $R_G$ may represent an alkyl, alkenyl, oxa-alkyl, oxa-alkenyl, aza-alkyl, aza-alkenyl, thia-alkyl, thia-alkenyl, aryl, alkylaryl, alkenylaryl, arylalkyl, arylalkenyl radical, an alicyclic radical or an aromatic radical possibly carrying at least one lateral chain comprising a heteroatom or possibly comprising at least one heteroatom in the cycle, said $R_E$ and $R_G$ may be halogenated or perhalogenated.

According to an embodiment, $R_E$ and $R_G$ are selected independently from one another from alkyl or alkenyl radicals having 1 to 12 carbon atoms and possibly comprising at least one heterotom O, N or S in the main chain or in a lateral chain, and carrying a hydroxy group, a carbonyl group, an amine group, a carboxyl group.

$R_E$ and $R_G$ may also be selected independently from one another from aryl, arylalkyl, alkylaryl or alkenylaryl radicals, in which the aromatic nuclei, possibly condensed, comprise heteroatoms such as nitrogen, oxygen, sulfur.

In a particular embodiment, one of the groups $R_E$ or $R_G$ may be a radical having an iodonium group, a sulfonium, oxonium, ammonium, amidinium, guanidinium, pyridinium, imidazolium, imidazolinium, traizolium, phosphonium or carbonium group, said ionic group totally or partially acting as cation M. The compound of the invention then constitutes a zwitterion.

When $R_E$ or $R_G$ includes at least one ethylenic unsaturation and/or a condensable group and/or a group which is thermally, photochemically or ionically dissociable, the compounds of the invention are reactive compounds which may be subject to polymerizations, cross-linkings or condensations, possibly with other monomers. They may also be used to fix ionophorous groups on polymers carrying the reactive function.

A substituent $R_E$ or $R_G$ may be a mesomorphous group, or a chromophore group or a self-doped electronically conducting polymer or a hydrolyzable alkoxysilane.

A substituent $R_E$ or $R_G$ may include a group capable of trapping free radicals such as for example a hindered phenol or a quinone.

A substituent $R_E$ or $R_G$ may also include a dissociating dipole such as, for example, an amide function, a sulfonamide function or a nitrile function.

A substituent $R_E$ or $R_G$ may also include a redox couple, for example a disulfide group, a thioamide group, a ferrocene group, a phenothiazine group, a bis(dialkylaminoaryl) group, a nitroxide group or an aromatic imide group.

A substituent $R_E$ or $R_G$ may include either a complexing ligand or an optically active group.

A substituent $R_E$—$Y_E$— represents an amino acid, or an optically or biologically active polypeptide.

According to another variant, a compound according to the invention comprises a substituent Z which represents a radical having a valency v higher than two, itself including at least one of the anionic aromatic heterocyclic groups

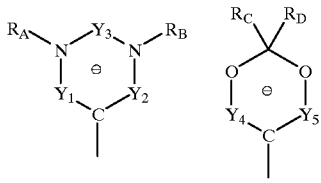

In this case, the negative charges present on the anionic part of the compound of the invention may be compensated by the appropriate number of cations or cationic ionophorous groups M.

According to a particular embodiment, the multivalent radical Z is a bivalent radical comprising at least one —$SO_2$—, one —CO— group, one perfluoroalkylene group having 2 to 8 carbon atoms, one phenylene group possibly substituted by heteroatoms, a redox group —$(W=W)_n$— or a cationic group —$(W=W)_n$—$W^+$—, in which W represents a nitrogen atom or a group —C(R)—, R representing an hydrogen atom or an organic radical and $0 \leq n \leq 5$. The presence of the cationic group —$(W=W)_n$—$W^+$— gives to the compound of the invention colouring properties which are very useful for lasers. R preferably has 1 to 8 carbon atoms, or two radicals R carried by adjacent carbon atoms forming a cycle. According to an embodiment, Z is part of a recurring unit of a polymer chain. The compound of the invention then presents polyelectrolyte properties.

$R_E$ or $R_G$ may also be part of a poly(oxyalkylene) radical or a polystyrene radical.

A compound of the present invention in which the anion corresponds to the above general formula A may be prepared according to the following reaction schemes:

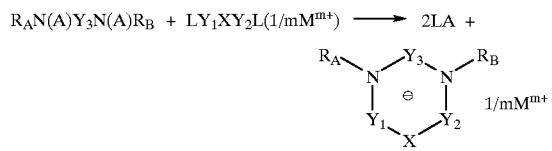

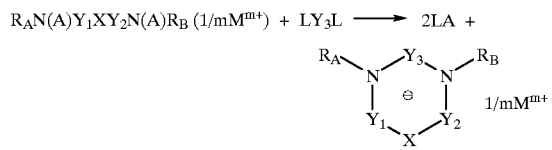

A compound of the present invention in which the anion corresponds to the above general formula B may be prepared by the following reaction scheme:

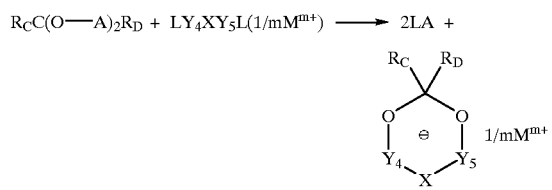

In all cases:

L represents a starting electronegative groups selected from F, Cl, Br, N-imidazoyl, N-triazoyl, $R_F$—O—, $R_FCH_2$—O— and $R_FSO_x$—, $R_F$ being a perfluoroalkyl radical;

A represents a cation $M^+$, a trialkyl-sylyl group, a trialkyl germanyl group, a trialkylstannyl group or a tertioalkyl group, in which the alkyl substituents have 1 to 6 carbon atoms.

It is advantageous in the case where A=G to permit a displacement of the reaction in the direction of the formation of the compound of the invention by addition of a tertiary or hindered base T capable of forming the salt $L^-[HT^+]$ by combination with the proton.

The preferred tertiary bases are in particular selected from alkylamines, for example triethylamine, di-isopropylethylamine, quinuclidine; 1,4 diazabicyclo[2,2,2]octane (DABCO); pyridines, for example pyridine, alkylpyridines, dialkylaminopyridines; imidazoles, for example N-alkylimidazoles, imidazo[1,2,-a]pyridine; amidines, for example 1,5 diazabicyclo[4,3,0]non-5-ene (DBN), 1,8 diazabicyclo[5,4,0]undec-7-ene (DBU); guanidines, for example tetramethyl guanidine, 1,3,4,7,8-hexahydro-1-methyl-2H-pyrimido[1,2-a]-pyrimidine (HPP).

The use of a compound $R_C$—C(O—A)$_2$—$R_D$ in which A is a tertioalkyl group is advantageous, since such a group is a proton precursor by formation of the corresponding alkene according to the reaction $(CH_3)_3C$—→$(CH_3)_2C$=$CH_2$+ H—.

The use of a compound $R_C$—C(O—A)$_2$—$R_D$ in which A is a trialkylsilyl group is especially interesting when the starting group is a fluorine atom, by reason of the very high stability of the bond F—Si.

In all these compounds, X represents —CH— or —C(Z)—. The compounds obtained with X=CH may then be modified by substitution of the residual proton, for example, by action of trifluoromethane sulfonic anhydride.

In the case where at least one of the $Y_i$ is a group—C(=NCN)— or a group —C(=C(CN)$_2$)—, the processes to obtain these groups are known to one skilled in the art. By way of example, the reaction of a carbonyl group with cyanamide or malononitrile may be mentioned.

The ionic compounds of the present invention comprise at least one ionophorous group on which substituents which may be quite diverse are fixed. Bearing in mind the large possible choice of substituents, the compounds of the invention enable to produce properties of ionic conduction in most liquid or polymer organic media having a polarity, even low. The applications are important in the field of electrochemistry, in particular for storing energy in primary or secondary generators, in supercapacitances, in combustible batteries and in electroluminescent diodes. The compatibility of the ionic compounds of the invention with polymers or organic liquids enable to produce noted antistatic properties, even when the content of ionic compound is extremely low. The compounds of the invention which are polymers, as well as polymeric compounds obtained from compounds of the invention having the property of self polymerization or copolymerization, have the above-mentioned properties with the advantage of having a fixed anionic charge. This is why another object of the present invention consists in an ionically conductive material consisting of an ionic compound of the present invention in solution in a solvent.

According to an embodiment, the ionic compound used for preparing an ionically conducting material is selected from compounds in which the cation is ammonium, or a cation derived from a metal, in particular, lithium or potassium, zinc, calcium, rare earth metals, or an organic cation, such as a substituted ammonium, an imidazolium, a triazolium, a pyridinium, a 4-dimethylamino-pyridinium, said cations possibly carrying a substituent on the carbon atoms of the cycle. The ionically conducting material thus obtained has an elevated conductivity and solubility in solvents, due to low interactions between the positive charge and the negative charge. Its range of electrochemical stability is wide, and it is stable in reducing as well as oxidizing media. Moreover, the compounds which have an organic cation and a melting point lower than 150° C., in particular compounds of imidazolium, triazolium, pyridinium, 4-dimethyl-amino-pyridinium have an intrinsic elevated conductivity, even in the absence of solvent, when they are in molten phase.

The properties of the ionically conducting material may also be adapted by the choice of substituents $R_A$, $R_B$, $R_C$, $R_D$, $R_E$ and $R_G$.

The choice for at least one of the substituents $R_A$, $R_B$, $R_C$, $R_D$, $R_E$ or $R_G$ of an alkyl group, an aryl group, an alkylaryl group or an arylalkyl group enables to induce in the ionically conductive material properties of the type mesogene, in particular alkyl groups of 6 to 20 carbon atoms, arylalkyl groups, in particular those containing a biphenyl unit which produce phases of the type liquid crystal. Properties of conduction in phases of the type liquid crystal, nematic, cholesteric or discotic, are interesting for applications relative to optical postings or to reduce the mobility of the anions in the electrolyte, in particular in polymer electrolytes, without affecting the mobility of the cations. This particularity is important for applications in electrochemical generators, in particular those involving lithium cations.

When Z is a mesomorphous group or a group comprising at least one ethylenic unsaturation and/or a condensable group and/or a group which is thermally, photochemically or ionically dissociable, the ionically conductive material easily forms polymers or copolymers which are polyelectrolytes, intrinsically when the polymer carries the solvating groups, or by addition or a polar solvent of the liquid or polymer type, or by mixture with such a solvent. These products have a conductivity which is solely due to the cations, which constitutes a very useful property for applications of the electrochemical generator type. When used in low molar fraction in a copolymer, they induce stable antistatic properties which are little dependent on humidity and promote the fixation of cationic colouring materials, this property being useful for textile fibers and lasers with colouring materials.

The presence of a substituent Z which is a self-doped electronically conductive polymer improves the stability of the ionically conductive material with respect to exterior agents. The conductivity is stable in time, even at elevated temperatures. In contact with metal, these materials give interface resistances which are very weak and in particular protect ferrous metals or aluminum against corrosion.

When a Z is a hydrolyzable alkoxysilane, the ionically conductive material may form stable polymers by the simple mechanism of hydrolysis-condensation in the presence of water, thereby enabling to treat surfaces of oxides, silica, silicates, in particular glass, to produce properties of surface conduction, antistatic properties, or to promote the adhesion of polar polymers.

When a substituent Z is a group comprising a free radical trap such as a hindered phenol, or a quinone, the ionically conductive material has the following advantages and properties: it acts as antioxidant with no volatility and is compatible with polar monomers and polymers, to which it additionally gives antistatic properties.

When Z comprises a dissociating dipole such as an amide, a sulfonamide or a nitrile, the ionically conductive material has an improved conductivity in media of low and medium polarity, in particular in solvating polymers which enables to minimize, even to suppress, the addition of solvents or volatile plasticizing agents.

The presence of a substituent Z which contains a redox couple such as a disulfide, a thioamide, a ferrocene, a phenothiazine, a group bis(dialkylaminoaryl), a nitroxide, an aromatic imide, enables to produce in the ionically conductive material, properties of a redox shuttle which are useful as an element of protection and equalization of charge of electrochemical generators, in photoelectrochemical systems, in particular for the conversion of light into electricity in systems of modulation of light of the electrochrome type.

The presence of a substituent Z which is a complexing ligand in an ionically conductive material enables to chelate metallic cations, in particular those which possess an elevated charge (2, 3 and 4), in the form of soluble complex in organic media, including in aprotic media, and enables the transport of these cations in particular in the form of anionic complex, in solvating polymers. The metallic cations of elevated charge are indeed immovable in solvating polymers. This type of complexing gives with certain cations of transition metals (Fe, Co . . . ) or certain rare earths (Ce, Eu . . . ) particularly stable redox couples.

The ionically conductive materials containing a compound of the invention in which at least one of the substituents $R_A$, $R_B$, $R_C$, $R_D$, $R_E$ or $R_G$ is an alkyl or alkenyl substituent which contains at least one heteroatom selected from O, N or S have a complexing and plasticizing capacity, in particular in polar polymers and especially polyethers. The heteroatoms N and S are selectively complexing for cations of transition metals, Zn and Pb.

When a substituent alkyl or alkenyl $R_E$ or $R_G$ additionally carries an hydroxy group, a carbonyl group, an amine group, a carboxyl group, an isocyanate group or a thioisocyanate group, the ionic compound of the invention may give by polycondensation a polymer or a copolymer and the ionically conductive material which contains such a polymer or copolymer has the properties of a polyelectrolyte.

The presence, in the ionically conductive material of the invention, of a compound in which a substituent $R_E$ or $R_G$ is selected from aryl, arylalkyl, alkylaryl, alkylaryl or alkenylaryl radicals, in which the lateral chains and/or the aromatic nuclei comprise heteroatoms such as nitrogen, oxygen, sulfur, improves dissociation and increases the possibility of forming complexes depending on the position of the heteroatom (pyridine) or the possibility to give by duplicative oxidation conjugated polymers or copolymers (pyrrole, thiophene).

When the ionically conductive material contains a compound of the invention in which a substituent Z represents a recurring unit of a polymer chain, the material constitutes a polyelectrolyte.

A compound of the invention in which the substituent Z is selected from the group consisting of $-OC_nF_{2n+1}$, $-OC_2F_4H$, $-SC_nF_{2n+1}$ and $-SC_2F_4H$, $-OCF=CF_2$, $-SCF=CF_2$, n being a whole number from 1 to 8, is a precursor of stable monomers and polymers, in particular towards oxygen even at temperatures higher than 80° C. when dealing with polymers. An ionically conductive material which contains such a compound is therefore particularly suitable as the electrolyte of a combustible battery.

An ionically conductive material of the present invention comprises an ionic compound of the present invention in solution in a solvent.

The solvent may be an aprotic liquid solvent, a polar polymer or a mixture thereof.

The aprotic liquid solvent is selected for example from linear ethers and cyclic ethers, esters, nitriles, nitro derivatives, amides, sulfones, sulfolanes, alkylsulfamides and partially halogenated hydrocarbons. The solvents which are particularly preferred are diethylether, dimethoxyethane, glyme, tetrahydrofurane, dioxane, dimethyltetrahydrofurane, methyl or ethyl formate, propylene or ethylene carbonate, alkyl carbonates (such as dimethyl carbonate, diethyl carbonate and methylpropyl carbonate), butyrolactones, acetonitrile, benzonitrile, nitromethane, nitrobenzene, dimethylformamide, diethylformamide, N-methylpyrrolidone, dimethylsulfone, tetramethylene sulfone and tetraalkylsulfonamides, having 5 to 10 carbon atoms.

The polar polymer may be selected from cross-linked or non-cross-linked solvating polymers, which may carry grafted ionic groups. A solvating polymer is a polymer which includes solvating units containing at least one heteroatom selected from sulfur, oxygen, nitrogen and fluorine. By way of example of solvating polymers, there may be cited polyethers of linear structure, comb or blocks, which may form a network, based on poly(ethylene oxide), or copolymers containing the unit ethylene oxide or propylene oxide or allylglycidylether, polyphosphazenes, cross-linked networks based on polyethylene glycol cross-linked with isocyanates or networks obtained by polycondensation and carrying groups which enable the incorporation of cross-linkable groups. Block copolymers in which certain blocks carry functions which have redox properties may also be cited. Of course, the above list is non-limiting, and all the polymers having solvating properties may be used.

An ionically conductive material of the present invention may simultaneously comprise an aprotic liquid solvent selected from the aprotic liquid solvents mentioned above and a polar polymer solvent comprising units containing at least one heteroatom selected from sulfur, nitrogen, oxygen and fluorine. It may comprise from 2 to 98% liquid solvent. By way of example of such a polar polymer, polymers which mainly contain units derived from acrylonitrile, vinylidene fluoride, N-vinylpyrrolidone or methyl methacrylate may be mentioned. The proportion of aprotic liquid in the solvent may vary from 2% (corresponding to a plasticized solvent) to 98% (corresponding to a gelled solvent).

An ionically conductive material of the invention may additionally contain a salt which is well known to be used in the prior art for preparing ionically conductive material. Among the salts which may be used in admixture with an ionic compound of the invention, a salt selected from perfluoroalcanesulfonates, bis(perfluoroalkylsulfonyl) imides, bis(perfluoroalkylsulfonyl)methanes and tris (perfluoroalkylsulfonyl)methanes are particularly preferred.

Of course, an ionically conductive material of the invention may additionally contain additives known to be used in this type of material and for example mineral or organic charges in the form of powder or fibers.

An ionically conductive material of the invention may be used as electrolyte in an electrochemical generator. Thus, another object of the present invention is an electrochemical generator comprising a negative electrode and a positive electrode both separated by an electrolyte, characterized in that the electrolyte is an ionically conductive material as defined above. According to a particular embodiment, such a generator comprises a negative electrode consisting of metallic lithium, or an alloy thereof, possibly in the form of nanometric dispersion in lithium oxide, or a double nitride of lithium and a transition metal, or an oxide of low potential having the general formula $Li_{1+y+x/3}Ti_{2-x/3}O_4$ ($0 \leq x \leq 1$, $0 \leq y \leq 1$), or carbon and carbonated products derived from the pyrolysis of organic materials. According to another embodiment, the generator comprises a positive electrode selected from vanadium oxides $VO_x$ ($2 \leq x \leq 2,5$), $LiV_3O_8$, $Li_yNi_{1-x}Co_xO_2$, ($0 \leq x \leq 1$; $0 \leq y \leq 1$), spinels of manganese $Li_yMn_{1-x}M_xO_2$ (M=Cr, Al, V, Ni, $0 \leq x \leq 0,5$; $0 \leq y \leq 2$), organic polydisulfides FeS, $FeS_2$, iron sulfate $Fe_2(SO_4)_3$, phosphates and phosphosilicates of iron and lithium of olivine structure, or substituted products wherein iron is replaced by manganese, used alone or in admixtures. The collector of the positive electrode is preferably aluminum.

An ionically conductive material of the present invention may also be used in a supercapacitance. Another object of the present invention is consequently a supercapacitance utilizing at least one carbon electrode of high specific surface, or an electrode containing a redox polymer in which the electrolyte is an ionically conductive material such as defined above.

An ionically conductive material of the present invention may also be used for doping p or n an electronically conductive polymer and this use constitutes another object of the present invention.

In addition, an ionically conductive material of the present invention may be used as an electrolyte is an electrochrome device. An electrochrome device in which the electrolyte is an ionically conductive material according to the invention is another object of the present invention.

It has been observed that the strong dissociation of ionic species of the compounds of the invention results in a stabilization of carbocations, in particular those in which there is a conjugation with oxygen or nitrogen and, surprisingly, by a strong activity of the proton form of the compounds of the invention on certain monomers. The present invention also has as an object the use of ionic compounds as photoinitiators as sources of Brønsted acid which are catalysts for the polymerization or cross-linking of monomers or prepolymers capable of cationic reaction, or as catalysts for the modification of polymers.

The process of polymerization or cross-linking of monomers or prepolymers capable of cationic reaction is characterized in that there is used a compound of the invention as photoinitiator constituting a source of acid catalyzing the polymerization reaction. The compounds according to the invention in which the cation is a group having a bond —N=N$^+$, —N=N—, a sulfonium group, an iodonium group, or an arene-ferrocenium cation which is substituted or non-substituted, possibly incorporated in a polymeric network, are particularly preferred.

The choice of the various substituents is made so as to increase the solubility of said compound in the solvents used for the reaction of monomers or prepolymers, and as a function of the desired properties for the final polymer. For example, the choice of non-substituted alkyl radicals gives a solubility in low polar media. The choice of radicals comprising an oxa group or a sulfone will give a solubility in polar media. The radicals including a sulfoxide group, a sulfone group, a phosphine oxide group, a phosphonate group, respectively obtained by the addition of oxygen on the atoms of sulfur or phosphorus, may give to the polymer obtained improved properties with respect to adhesion, shine, resistance to oxidation or to UV. The monomers and prepolymers which may be polymerized or cross-linked with the photoinitiators of the present invention are those which may undergo a cationic polymerization.

Among the monomers, those which include a cyclic ether function, a cyclic thioether function or cyclic amine function, vinyl compounds (more particularly vinyl ethers), oxazolines, lactones and lactames may be mentioned.

Among the polymers of the ether or cyclic thioether type, ethylene oxide, propylene oxide, oxetane, epichlorhydrin, tetrahydrofurane, styrene oxide, cyclohexene oxide, vinylcyclohexene oxide, glycidol, butylene oxide, octylene oxide, glycidyl ethers and esters (for example glycidyl methacrylate or acrylate, phenyl glycidyl ether, diglycidylether of bisphenol A or its fluorinated derivatives), cyclic acetals having 4 to 15 carbon atoms (for example dioxolane, 1,3-dioxane, 1,3-dioxepane) and spiro-bicyclo dioxolanes may be mentioned.

Among vinyl compounds, vinyl ethers constitute a very important family of monomers which are capable of cationic polymerization. By way of example, there may be mentioned ethyl vinyl ether, propyl vinyl ether, isobutyl vinyl ether, octadecyl vinyl ether, ethyleneglycol monovinyl ether, diethyleneglycol divinyl ether, butanediol monovinyl ether, butanediol divinyl ether, hexanediol divinyl ether, ethyleneglycol butyl vinyl ether, triethyleneglycol methyl vinyl ether, cyclohexanedimethanol monovinyl ether, cyclohexanedimethanol divinyl ether, 2-ethylhexyl vinyl ether, poly-THF-divinyl ether having a molecular weight between 150 and 5,000, diethyleneglycol monovinyl ether, trimethylolpropane trivinyl ether, aminopropyl vinyl ether, 2-diethylaminoethyl vinyl ether.

Other vinyl compounds may include, by way of example, 1,1-dialkylethylenes (for example isobutene), vinyl aromatic monomers (for example styrene, α-alkylstyrenes, such as α-methylstyrene, 4-vinylanisole, acenaphthene) N-vinyl compounds (for examples N-vinylpyrolidone or N-vinyl sulfonamides).

Among prepolymers, there may be mentioned compounds in which epoxy groups are carried by an aliphatic chain, an aromatic chain, or a heterocyclic chain, for example glycidic ethers of bisphenol A which are ethoxylated by 3 to 15 ethylene oxide units, siloxanes having lateral groups of the epoxycyclohexene-ethyl type obtained by hydrosilylation of copolymers of dialkyl, alkylaryl or diaryl siloxane with methyl hydrogenosiloxane in the presence of vinylcyclohexene oxide, condensation products of the sol-gel type obtained from triethoxy or trimethoxy silapropylcyclohexene oxide, urethanes incorporating the reaction products of butanediol monovinylether and an alcohol of a functionality higher than or equal to 2 with an aliphatic or aromatic di- or tri-isocyanate.

The process of polymerization according to the invention consists in mixing at least one monomer or prepolymer capable of cationic polymerization and at least one ionic compound of the invention, and subjecting the mixture obtained to actinic or β radiation. Preferably, the reaction mixture is subjected to radiation after having been formed into a thin layer having a thickness lower than 5 mm, preferably in the form of a thin layer having a thickness lower than or equal to 500 μm. The duration of the reaction depends on the thickness of the sample and the power of the source at the active λ wavelength. It is defined by the speed at which it passes in front of the source, which is between 300 m/min and 1 cm/min. Layers of the final material having a thickness higher than 5 mm may be obtained by repeating many times the operation consisting in spreading a layer and treating it with radiation.

Generally, the quantity of photoinitiator used is between 0.01 and 15% by weight with respect to the weight of the monomer or prepolymer, preferably between 0.1 and 5% by weight.

An ionic compound of the present invention may be used as photoinitiator in the absence of solvent, for example when it is intended to polymerize liquid monomers in which the ionic compound used as photoinitiator is soluble or easily dispersible. This type of utilization is particularly interesting, since it enables to overcome the problems associated with solvents (toxicity, flammability).

An ionic compound of the present invention may also be used as photoinitiator in the form of a homogeneous solution in a solvent which is inert towards polymerization, ready to be used and easily dispersible, in particular in the case where the medium to be polymerized or cross-linked has a high viscosity.

As example of an inert solvent, there may be mentioned volatile solvents, such as acetone, methyl-ethyl ketone and acetonitrile. These solvents will be used merely to dilute the products to be polymerized or cross-linked (to make them less viscous, especially when dealing with a prepolymer). They will be removed by drying after polymerization or cross-linking. Non-volatile solvents may also be mentioned. A non-volatile solvent also serves to dilute the products that one wishes to polymerize or cross-link, and to dissolve the ionic compound of the invention used as photoinitiator, however, it will remain in the material formed and will thus act as plasticizing agent. By way of example, propylene carbonate, γ-butyrolactone, ether-esters of mono-, di-, tri-ethylene or propylene glycols, ether-alcohols of mono-, di-, tri-ethylene or propylene glycols, plasticizing agents such as esters of phthalic acid or citric acid may be mentioned.

According to another embodiment of the invention, there may be used as solvent or diluent a compound which is reactive towards polymerization, which is a compound of low molecular weight and of low viscosity which will simultaneously act as polymerization monomer and solvent or diluent for more viscous polymers or prepolymers used in combination. After the reaction, these monomers having been used as solvent will be part of the macromolecular network finally obtained, their integration being wider when dealing with bi-functional monomers. The material obtained after irradiation is now free of products having a low molecular weight and a substantial vapour tension, or capable of contaminating objects with which the polymer is in contact. By way of example, a reactive solvent may be selected from mono and divinyl ethers of mono-, di-, tri-, tetra-ethylene and propylene glycols, N-methylpyrolidone, 2-propenylether of propylene carbonate commercially available for example under the commercial designation PEPC from ISP, New Jersey, United States.

To irradiate the reaction mixture, the irradiation may be selected from ultraviolet radiation, visible radiation, X-rays, γ rays and β radiation. When ultraviolet light is used as actinic radiation, it may be advantageous to add to the photoinitiators of the invention photosensitizers intended to provide an efficient photolysis with wavelengths less energetic than those corresponding to the maximum of absorption of the photoinitiator, such as those produced by industrial devices, (1≈300 nm for mercury vapour lamps in particular). Such additives are known, and by way of non-limiting example, there may be mentioned anthracene, diphenyl-9,10-anthracene, perylene, phenothiazine, tetracene, xanthone, thioxanthone, acetophenone, benzophenone, 1,3,5-triaryl-2-pyrazolines and derivatives thereof, in particular derivatives which are substituted on the aromatic nuclei by alkyl, oxa- or aza-alkyl radicals, enabling inter alia to change the absorption wavelength. Isopropylthioxantone is an example of preferred photosensitizer when an iodonium salt according to the invention is used as photoinitiator.

Among the different types of radiation mentioned, ultraviolet radiation is particularly preferred. On the one hand, it is more convenient to use than the other radiations mentioned. On the other hand, photoinitiators are in general directly sensitive towards UV rays and photosensitizers are more efficient when the difference of energy (δλ) is lower.

The ionic compounds of the invention may also be used in association with free radical initiators produced thermally or by action of actinic radiation. It is also possible to polymerize or cross-link mixtures of monomers or polymers containing functions in which the types of polymerization are different. For example, monomers or prepolymers which polymerize by free radical and monomers or prepolymers which polymerize by cationic polymerization. This possibility is particularly advantageous to produce interpenetrated networks having physical properties which are different from those which would be obtained by a simple mixture of polymers originating from corresponding monomers. Vinyl ethers are not or are very little active by free radical initiation. It is therefore possible, in a reaction mixture containing a photoinitiator according to the invention, a free radical initiator, at least one monomer of the vinyl ether type and at least one monomer comprising non-activated double bonds such as those of the allyl groups, to carry out a separate polymerization of each type of monomer. On the other hand, it is known that monomers which are lacking in electrons, such as esters or amides of furmaric acid, maleic acid, acrylic or methacrylic acid, itaconic acid, acrylonitrile, methacrylonitrile, maleimide and derivatives thereof, form in the presence of vinyl ethers which are enriched in electrons, complexes of transfer of charge giving alternated polymers 1:1 by free radical initiation. An initial excess of vinyl monomers with respect to this stoichiometry enables to preserve polymerizable functions by pure cationic initiation. The start of the activity of a mixture of free radical initiator and cationic initiator according to the invention may be carried simultaneously for the two reactants in the case for example of isolation by actinic radiation of a wavelength for which the photoinitiators of the invention and the selected radical initiators are active, for example at 1=250 nm. By way of example, the following commercial products: Irgacure 184®, Irgacure 651®, Irgacure 261®, Quantacure DMB®, Quantacure ITX® may be mentioned as initiators.

It may also be advantageous to use the two types of polymerization in a sequential manner, to first form prepolymers which are easy to shape and in which hardening, adhesion, solubility as well as degree of cross-linking may be modified by initiating the activity of the cationic initiator. For example, a mixture of a thermo-dissociable radical initiator and a cationic photoinitiator according to the invention enables to provide sequential polymerizations or cross-linking, first under the action of heat, then under the action of actinic radiation. Similarly, if a free radical initiator and a cationic photoinitiator according to the invention are selected, the first being photosensitive at longer wavelengths than the one initiating the photoinitiator according to the invention, there is obtained a cross-linking in two controllable steps. Free radical initiators may for example be Irgacure® 651 enabling to initiate free radical polymerizations at wavelength of 365 nm.

The invention also has as an object the use of ionic compounds of the invention for chemical amplification reactions of photoresists in the field of microlithography. During such use, a film of a material comprising a polymer and an ionic compound of the invention is subject to irradiation. The irradiation causes the formation of the acid by replacement of the cation M with a proton, which catalyzes the decomposition or transformation of the polymer. After decomposition or transformation of the polymer on the parts of the film which have been irradiated, the monomers formed or the polymer which has been converted are removed and what remains is an image of the unexposed parts. For this particular application, it is advantageous to use a compound of the invention which is in the form of a polymer consisting essentially of styrenyl recurring units carrying as substituent an aromatic anionic heterocycle. These compounds enable to obtain after photolysis products which are not volatile, and therefore not odoriferous when dealing with sulfides. Among the polymers which may thus be modified in the presence of a compound of the invention, there may for example be cited polymers containing ester units or tertiaryalkyl arylether units, for example poly (phthaldehydes), polymers of bisphenol A and a diacide, polytertiobutoxycarbonyl oxystyrene, polytertiobutoxy-a-methyl styrene, polyditertiobutylfumarate-co-allyltrimethyl-silane and polyacrylates of a tertiary alcohol, in particular tertiobutyl polyacrylate. Other polymers are described in J. V. Crivello et al, Chemistry of Materials 8, 376–381, (1996).

The ionic compounds of the present invention, which have an elevated thermal stability, give numerous advantages with respect to the known salts of the prior art. They have speeds of initiation and propagation which are comparable or higher than those obtained with coordination anions of the type $PF_6^-$, $AsF_6^-$ and especially $SbF_6^-$.

In the compounds of the present invention, the pairs of ions have a very high dissociation, which enables the expression of intrinsic catalytic properties of the cation $M^{m+}$, in which the active orbits are easily exposed to substrates of the reaction, especially in different media. Most of the important reactions of organic chemistry may thus be carried out under easy conditions, with excellent yields and the possibility of separating the catalyst from the reaction mixture. The demonstration of asymmetric induction by the use of an ionic compound according to the invention which carries a chiral group is particularly important in view of its generality and its ease of operation. The present invention consequently has as another object the use of compounds of the invention as catalysts in Friedel-Crafts reactions, Diels-Alder reactions, aldolization reactions, additions of Michael, reactions of allylation, reactions of pinacolic coupling, reaction of glycosilation, reaction of openings of the cycle of oxetanes, reactions of metathesis of alkenes, polymerizations of the Ziegler-Natta type, polymerizations of the metathesis type by cycle opening and polymerizations of the metathesis type of acyclic dienes. The preferred ionic compounds of the invention for utilization as catalyst for the above reactions are those in which the cation is selected from lithium, magnesium, copper, zinc, tin, trivalent metals, including rare earths, platinoids, and their organometallic couples, in particular metallocenes.

The compounds of the invention may also be used as solvent to carry out chemical, photochemical, electrochemical, photoelectrochemical reactions. For this particular use, the ionic compounds in which the cation is an imidazolium, triazolium, pyridinium or 4-dimethylaminopyridinium, are preferred, said cation possibly carrying a substituent on the carbon atoms of the cycle. Among the compounds being used in liquid form, those having a melting point lower than 150° C., more particularly lower than 100° C., are particularly preferred.

The inventors have also found that the anionic charge carried by the pentacyclic group or the group derived from tetrazapentalene exerts a stabilizing effect on electronic conductors of the conjugated polymer type, and that use of a compound in which one of the substituents comprises a long alkyl chain enables to make these polymers soluble in the usual organic solvents even in doped state. Grafting of these charges on the polymer itself gives polymers in which the global charge is cationic, which are soluble in organic solvents and have, in addition to their stability, properties of anticorrosion towards metals, aluminum and ferrous metals. It is also an object of the present invention to provide electronically conductive material comprising an ionic compound of the present invention in which the cationic part is a polycation constituted of a doped "p" conjugated polymer. The preferred ionic compounds for this application are those in which one of the substituents $R_A$, $R_B$, $R_C$, $R_D$, or Z contains at least one alkyl chain having 6 to 20 carbon atoms.

The colouring materials of cationic type (cyanines) are used more and more frequently as sensitizers of photographic films, for storing optical information (optical disks accessible in writing), for lasers. The tendency of these conjugated molecules to pile over one another when they are in solid phase limits their utilization, because of the variation of the optical properties with respect to the isolated molecule. The use of ionic compounds of the invention for manufacturing cationic colouring materials in which the counter ions, possibly bound to this same molecule, correspond to functions of the invention enables to reduce phenomenon of aggregation, including in solid polymer matrices and to stabilize these colouring materials. It is another object of the present invention to provide a composition of cationic colouring material, characterized in that it contains an ionic compound according to the invention. Particularly preferred ionic compounds for this application are those in which the negative charge(s) of the ionic group are either fixed to the molecule of the colouring material, or they constitute the counter-ion of the positive charges of the colouring material. Other preferred compounds for this application are those in which the radical Z is a bivalent radical comprising at least one cationic group —(W=W)$_n$—W$^+$—, in which W represents a nitrogen atom or a —C(R)— group (R being an organic radical) and $0 \leq n \leq 5$.

The present invention is illustrated by the following examples to which it is however not limited.

EXAMPLE 1

To 9.91 g (100 mmoles) of butyl isocyanate $C_4H_9NCO$ in 30 ml of anhydrous dichloromethane, there is added drop wise, during 30 min, 5.91 g (100 mmoles) of propylamine $C_3H_7NH_2$ diluted in 20 ml of anhydrous dichloromethane. After 2 hours, 14.1 g (100 mmoles) of malonyl chloride $ClCOCH_2COCl$ in 100 ml of anhydrous dichloromethane were added at 0° C. under argon. A release of hydrochloric acid accompanying the reaction of cyclization was noted. After 48 hours, the solution was evaporated and 1-propyl-3-dibutyl-barbituric acid was recovered in quantitative yield after drying.

To 11.3 g (50 mmoles) of this compound in solution in 60 ml of anhydrous tetrahydrofurane (THF), at −20° C. and under mechanical stirring, there is added 11.22 g (100 mmoles) of 1,4-diaza-bicyclo[2,2,2]octane (DABCO), and drop wise 8.43 g (100 mmoles) of trifluoromethanesulfonyl chloride $CF_3SO_2Cl$. After 24 hours, the reaction mixture was stirred during 4 hours with 2.12 g (50 mmoles) of anhydrous lithium chloride. After filtering to remove the precipitate of DABCO hydrochloride, the solvent was evaporated. After drying, the lithium salt of 5-trifluoromethanesulfonyl-1-propyl-3-butyl-barbituric was recovered in quantitative yield, with a purity determined by a proton RMN higher than 97%.

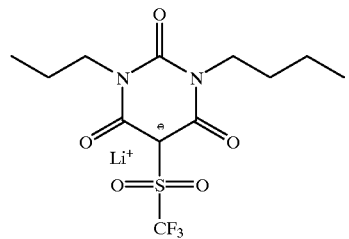

In the same manner, 5-trifluoromethanesulfonyl-1-allyl-3-butyl-barbituric acid was obtained by replacing propylamine with allylamine.

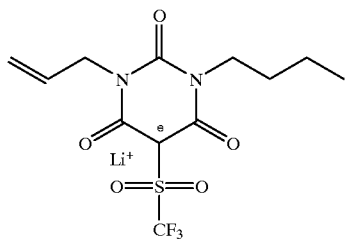

These salts are soluble in most of the usual organic solvents (tetrahydrofurane, acetonitrile, dimethylformamide, ethyl acetate, glymes, . . . ) and in aprotic solvating polymers such as polyethylene oxide. In the latter solvent at a concentration O/Li of 12/1, they show an ionic conductivity higher than $10^{-4}$ S.cm$^{-1}$ at a temperature of 60° C.

EXAMPLE 2

134.96 g (1 mole) of sulfuryl chloride $ClSO_2Cl$ diluted in 100 ml of anhydrous dichloromethane were added drop wise during 1 hour to a solution of 146.23 g (1 mole) of butylamine $C_4H_9NH_2$ (2 moles) in 500 ml of anhydrous THF at 0° C. The reaction was continued during 2 hours at 0° C., and during 3 hours at room temperature. After filtering the reaction mixture to remove the butylamine hydrochloride formed, the solvent was evaporated by means of a rotary evaporator. The product obtained was recrystallized in 200 ml of methanol, and 151 g of N,N'-dibutylsulfamide $C_4H_9NHSO_2NHC_4H_9$ (yield 72%) were recovered after filtration and drying, with a purity characterized by a proton RMN higher than 99%. To 20.83 g (100 mmoles) of N,N'-dibutylsulfamide and 10.41 g (100 mmoles) of malonic acid in 100 ml of anhydrous acetonitrile at 0° C., there is added 41.27 g of 1,3-dicyclohexylcarbodiimide (200 meq). After 2 hours at 0° C. and 24 hours at room temperature, the reaction mixture was filtered to remove the 1,3-dicyclohexylurea formed, and the solvent was evaporated. The product obtained was recrystallized in 50 ml of methanol containing 9.81 g (100 meq) of potassium acetate. After filtering and drying, 21.7 g of the potassium salt of 1,3-dibutyl-2-sulfonyl-barbituric (yield 69%) were recovered, with a purity characterized by a proton RMN higher than 98%.

1,3-dibutyl-2-sulfonyl-barbituric acid was prepared by ether extraction of the potassium salt in water at a pH lower than 2. Then, by a procedure similar to the one described in Example 1, the lithium salt of 5 -trifluoromethanesulfonyl-1,3-dibutyl-2-sulfonyl-barbituric acid and the lithium salt of 5-perfluorobutanesulfonyl-1,3-dibutyl-2-sulfonyl-barbituric acid were obtained by replacing trifluoromethanesulfonyl chloride with perflurobutanesulfonyl fluoride.

Potassium salts were obtained by recrystallizing lithium salt in a saturated solution of potassium chloride.

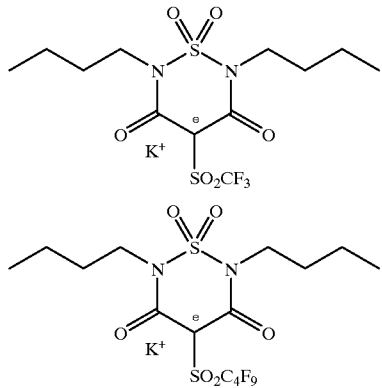

These salts are soluble in most of the usual organic solvents (tetrahydrofurane, acetonitrile, dimethylformamide, ethyl acetate, glymes, . . . ) and in aprotic solvating polymers such as polyethylene oxide. In the latter solvent, at a concentration O/Li of 12.1, they show an ionic conductivity higher than $2 \times 10^{-4}$ S.cm$^{-1}$ at a temperature of 60° C. The lithium salts, at a concentration as low as 0.1 g/l in water, decrease the surface tension to a value lower than 25 mN/m.

EXAMPLE 3

16.02 g (100 mmoles) of ethyl malonate $C_2H_5OOCCH_2COOC_2H_5$ were reacted with 11.82 g (200 mmoles) of propylamine $C_3H_7NH_2$. After stirring the solution during 24 hours, there is obtained a thick paste which, after drying, has given a quantitative yield of dipropylamide malonate $C_3H_7NHOCCH_2CONHC_3H_7$ characterized by a proton RMN. There is then added drop wise 6.75 g (50 mmoles) of sulfuryl chloride $ClSO_2Cl$ diluted in 20 ml of anhydrous dichloromethane to 9.31 g of dipropylamide malonate (50 meq) in solution in 30 ml of pyridine at 0° C. The reaction was continued during two hours at room temperature, and during 48 hours at room temperature and the solvent was evaporated. The product obtained was reclaimed in 30 ml of water which has been acidified with 30 ml of hydrochloric acid 4 M, and extracted twice with 25 ml of ether. After drying the organic phase with magnesium sulfate, evaporating ether and drying the residue, 11.67 g (94% yield) of 1,3-dipropyl-2-sulfonyl-barbituric acid were recovered with a purity characterized by a proton RMN higher than 97%.

The potassium salt was obtained by treating the acid with potassium carbonate in water.

In 20 ml of anhydrous acetonitrile containing 2.12 g (20 mmoles) of bromine cyanide BrCN, there is added 2.87 g (20 mmoles) of silver chloride AgCl, then 20 mmoles of 1,3-dipropyl-2-sulfonyl-barbituric acid and 4.49 g (40 mmoles) of 1,4-diazabicyclo[2.2.2]octane (DABCO). After 24 hours, the solvent was evaporated and the residue was recrystallized in a saturated aqueous solution of potassium chloride. After filtering and drying, the following compound was obtained:

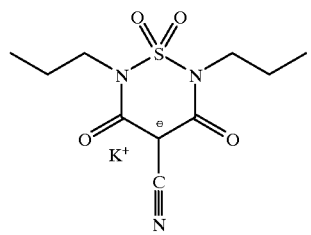

By a similar process, 1,3-di trifluoroethyl-2-sulfonyl-barbituric and its potassium salt, and the potassium salt of 5-cyano-1,3-di trifluoroethyl-2-sulfonyl-barbituric acid were obtained by replacing propylamine by trifluoroethylamine.

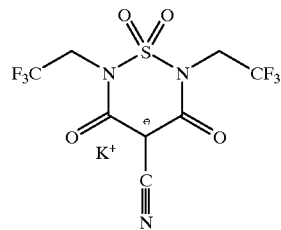

These salts are soluble in most of the usual organic solvents (tetrahydrofurane, acetonitrile, dimethylformamide, ethyl acetate, glymes, . . . ) and in aprotic solvating polymers such as polyethylene oxide. In the latter solvent at a concentration of O/Li of 12/1, they show an ionic conductivity higher than $10^{-3}$ S.cm$^{-1}$ at a temperature of 100° C.

EXAMPLE 4

10.12 g (100 mmoles) of 3-amino-1-propanol vinyl ether $CH_2=CHO(CH_2)_3NH_2$ in 30 ml of anhydrous THF were reacted with 9.91 g (50 mmoles) of 1,1'-sulfonyldiimidazole, prepared by reacting imidazole with sulfuryl chloride. After 48 hours, the reaction mixture was poured into a flask containing 8.01 g (50 mmoles) of ethyl malonate $C_2H_5O$—$OCCH_2CO$—$OC_2H_5$ and 8.1 g (75 mmoles) of sodium methoxide $CH_3ONa$. After 96 hours at room temperature, the solvents were evaporated and a product was reclaimed in 30 ml of methanol. After adding 4.91 g (50 mmoles) of potassium acetate (50 meq), a precipitate was formed which was recovered by filtration on a fritted glass of porosity N°3, and washed twice with 5 ml of cold water. 11.61 g of the potassium salt of 1,3-vinyloxypropyl-2-sulfonyl-barbituric acid were obtained after drying (69% yield) characterized by a proton RMN To 3.7 g (10 mmoles) of this compound in solution in 20 ml of THF at −20° C., there is added 2.01 g (10 mmoles) of 1-(trifluoromethanesulfonyl)imidazole (commercially available from Fluka). The reaction was continued during 4 hours at −20° C., and during 48 hours at room temperature. The solvent was then evaporated and the solid residue was washed with dichloromethane to remove the imidazole formed during the reaction. The following compound was obtained:

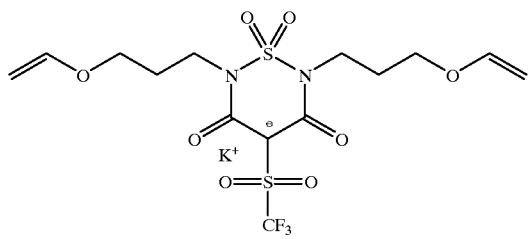

On the other hand, 3.7 g (10 mmoles) of the potassium salt of 1,3-vinyloxypropyl-2-sulfonyl-barbituric were treated with 1.96 g (10 mmoles) of 2,2,2-trifluoroethyl trifluoroacetate in 15 ml of anhydrous THF. After 24 hours, the solution obtained was evaporated and after drying, the potassium salt of 5-trifluoroacetyl-1,3-vinyloxypropyl-2-sulfonyl-barbituric acid was recovered in quantitative yield.

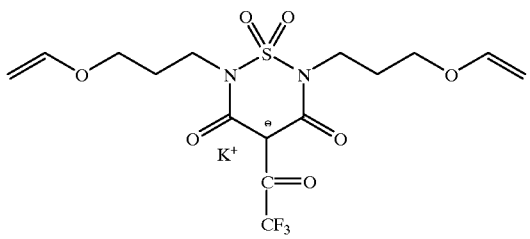

The homopolymers of these salts prepared by polymerization in anhydrous acetonitrile, initiated by cationic means with bis(trifluoromethanesulfonyl)imide, have a conductivity at a concentration of 0.8 M in a mixture of dimethylcarbonate and ethylene carbonate (2:1) higher than $10^{-3}$ S.cm$^{-1}$ at 30° C. Moreover, these homopolymers are soluble in most of the usual organic solvents (tetrahydrofurane, acetonitrile, dimethylformamide, ethyl acetate, glymes, . . . ) and in aprotic solvating polymers such as polyethylene oxide.

EXAMPLE 5

In 20 ml of anhydrous THF at −20° C. there is added 29.26 g (40 mmoles) of butylamine and drop wise 23.7 g (20 mmoles) of chloroflurosulfone $FSO_2Cl$. After 1 hour, 19.81 g of 2,2,-trifluoroethylamine $CF_3CH_2NH_2$ (20 mmoles) and 2 ml of pyridine were added, and the reaction was continued during 2 hours at −20° C. and for 48 hours at room temperature. The reaction mixture was filtered and the solvent was evaporated. After recrystallization of the residue in methanol, N-2,2,2-trifluoroethyl-n'-butyl-sulfamide was recovered. By a similar process, N-2,2,3,3,3-pentafluoropropyl-N'-butyl-sulfamide was prepared by replacing 2,2,2-trifluoroethylamine with 2,2,3,3,3-pentafluoropropylamine, and N-2,2,3,3,4,4,4-heptafluorobutyl-N'-butyl-sulfamide was prepared by replacing 2,2,2-trifluoroethylamine with 2,2,3,3,4,4,4-heptafluorobutylamine.

Barbituric acids and potassium salts corresponding to these three compounds were obtained by a process similar to the one described in Example 2.

Potassium salts of acids carrying a trifluoromethanesulfonyl group in C-5 were obtained by a process similar to the one described in Example 4.

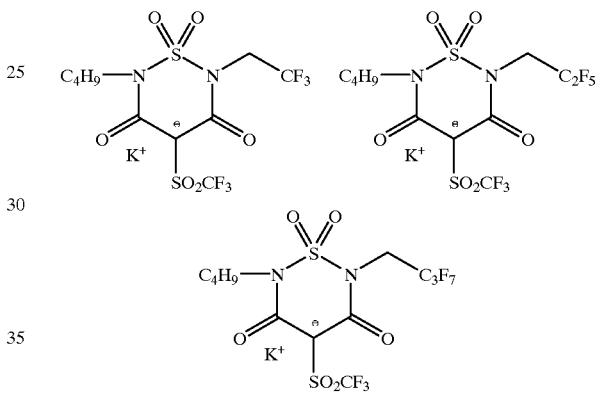

These salts are soluble in most of the usual organic solvents (tetrahydrofurane, acetonitrile, dimethylformamide, ethyl acetate, glymes, . . . ) and in aprotic solvating polymers.

EXAMPLE 6

By a process similar to Example 3, 5-fluoro-1,3-dibutyl-barbituric acid was obtained by replacing ethyl malonate with diethyl fluoromalonate (commercially available from Lancaster). The potassium salt was obtained by dosing the acid with a titrated solution of potassium hydroxide, the point of equivalency being obtained by pH metry. After lyophilization and drying under vacuum, the following compound was obtained in quantitative yield.

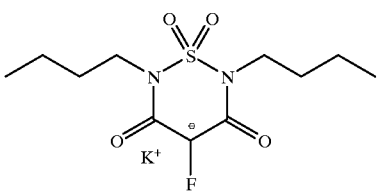

By a similar process, 5-fluoro-1,3-di-(2-ethylhexyl)-barbituric acid was obtained by replacing butylamine with 2-ethylhexylamine.

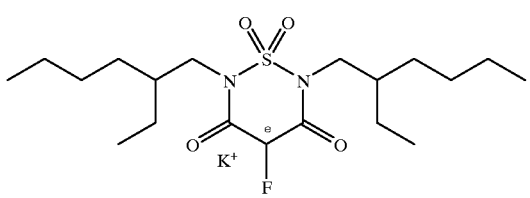

EXAMPLE 7

Chloro-bis(chlorosulfonyl)-methide ClCH(SO$_2$Cl)$_2$ was prepared by the method described by Fild & Rieck (*Chem.-Ztg.*, (1976), 100(9), 391–2) by reacting chloroacetic acid with phosphoryl chloride POCl$_3$. In 40 ml of dichloromethane, there is added 6.25 g (30 mmoles) of N,N'-dibutylsulfamide, obtained as in Example 2, and 7.42 g of chloro-bis(chlorosulfonyl)methide. After 48 hours under stirring, dichloromethane was evaporated and the residue was reclaimed in 40 ml of water. The lithium salt was obtained by dosing the acid with a titrated solution of lithium hydroxide, the point of equivalency being determined by pH-metry, after lyophilization and drying under vacuum, the following compound was obtained in quantitative yield:

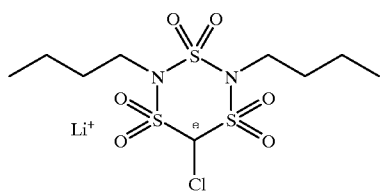

EXAMPLE 8

To 200 ml of anhydrous dichloromethane at −20° C., under mechanical stirring and in an atmosphere of argon, containing 20.81 g (200 mmoles) of malonic acid HOOCCH$_2$COOH and 41.63 g (200 mmoles) of hexafluoroacetone trihydrate CF$_3$COCF$_3$•3H$_2$O (commercially available from Aldrich), there is slowly added 95.17 g (800 mmoles) of thionyl chloride SOCl$_2$ diluted with 100 ml of anhydrous dichloromethane. When the addition was terminated (about 2 hours), the reaction was continued during 24 hours at −20° C. and for 24 hours at room temperature. The solvent was then evaporated and the residue was reclaimed in 100 ml of water. There is then added in portions 15.2 g (110 mmoles) of anhydrous potassium carbonate and the precipitate obtained was recrystallized after adding 14.91 g (200 mmoles) of anhydrous potassium chloride KCl. After filtering and drying, 35.8 g (71% yield) of the potassium salt of 2,2-trifluoromethyl-1,3-dioxolane-4,6-dione (I) were recovered, having a purity determined by a proton RMN higher than 98%.

The lithium salt was obtained by ionic exchange (metathesis) with lithium chloride in THF.

By a similar process except that one single equivalent of thionyl chloride was used, there is obtained:

the potassium salt of 2-methyl-2-trifluoromethyl-1,3-dioxolane-4,6-dione (II), by replacing hexafluoroacetone with 1,1,1-trifluoroacetone (98% purity and 65% yield), the potassium salt of 2-methyl-2-hepta-fluoropropyl-2,3-dioxolane-4,6-dione (III), by replacing hexafluoroacetone with 3,3,4,4,5,5,5-heptafluoro-2-pentanone (97% purity and 71% yield), and the potassium salt of 2-phenyl-2-trifluoromethyl-1,3-dioxolane-4,6-dione (IV), by replacing hexafluoroacetone with 2,2,2-trifluoroacetophenone (99% purity and 76% yield).

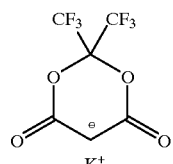
(I)

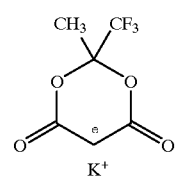
(II)

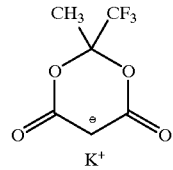
(III)

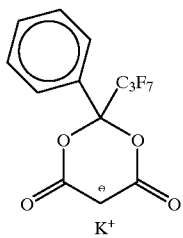
(VI)

The corresponding acids were prepared by extracting an acid solution of the salts with ether.

The potassium salts of the acids carrying a nitrile group in C-5 were prepared by a process similar to the one described in Example 3.

The potassium salts of the acids carrying a group trifluoromethanesulfonyl in C-5 were obtained by a process similar to the one described in Example 1, the potassium salts of the acids carrying a 4-styrenesulfonyl in C-5 were prepared by a process similar to the one described in Example 1, by replacing trifluoromethanesulfonyl chloride with 4-styrenesulfonyl chloride (commercially available from Dajac Monomers & Polymers; the potassium salts of acids carrying a perfluorobutanesulfonyl group in C-5 were prepared by replacing trifluoromethanesulfonyl chloride with perfluorobutane sulfonyl fluoride; the potassium salts of acids carrying a perfluorobutanesulfonyl group in C-5 were prepared by replacing trifluoromethanesulfonyl chloride with perfluorobutane sulfonyl fluoride; and the potassium salts of acids carrying a vinyl sulfonyl group in C-5 were prepared by replacing trifluoromethanesulfonyl chloride with ethylenesulfonyl fluoride (commercially available from ACROS).

In all cases, lithium salts were obtained by ionic exchange (metathesis) between potassium salts and lithium chloride in THF.

EXAMPLE 9

5.38 g (20 mmoles) of dodecylsulfonic acid chloride $C_{12}H_{25}SO_2Cl$ (commercially available from Lancaster) in 30 ml of anhydrous THF and 10 ml of pyridine were added to 6.29 g (20 mmoles) of the potassium salt of 1,3-dibutyl-2-sulfonyl-barbituric acid, prepared under conditions similar to those described in Example 2. After 24 hours, the slightly coloured solution was filtered to remove the precipitate of potassium chloride, and contacted with 800 mg of lithium carbonate $Li_2CO_3$ and 4 g of activated charcoal. The mixture was stirred during 24 hours, and the excess carbonate and the active carbon were removed by filtering the solution and the solvent was evaporated. 10.9 g of the lithium salt of 5-dodecylsulfonyl-1,3-dibutyl-2-sulfonylbarbituric acid were obtained in quantitative yield and the product is characterized by a proton RMN:

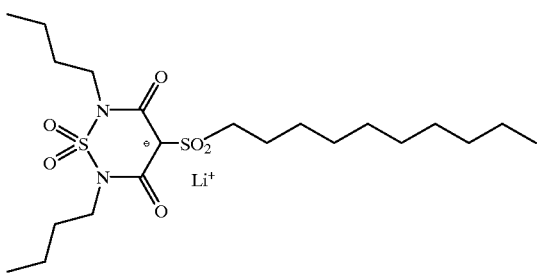

which has noted tensio-active properties, including in aprotic solvents and more particularly in aprotic solvating polymers.

EXAMPLE 10

479 mg (1 mmole) of Rhodamine B were suspended in 10 ml of pyridine and 314 mg (1 mmole) of the potassium salt of 1,3-dibutyl-2-sulfonylbarbituric acid, obtained in Example 2, and 206 mg (1 mmole) of dicyclohexylcarbodiimide were added. After 48 hours under stirring, the mixture was filtered to remove dicyclohexylurea and was subjected to evaporation. The compound obtained is a zwitterion:

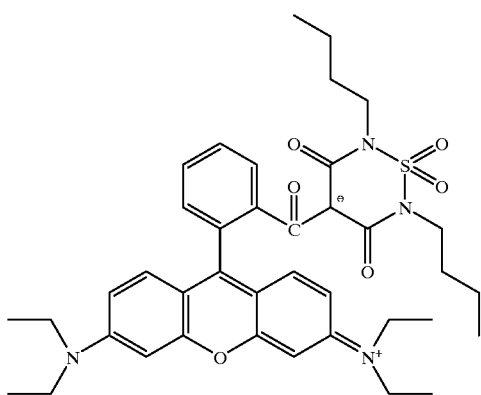

which has intense colouring properties. It is soluble in polar polymers and enables the production of lasers with colouring materials. The anionic group grafted on Rhodamine B also enables to be adsorbed on oxides, in particular non-particular titanium dioxide, it then acts as a sensitizer towards visible radiation, in particular in applications to photovoltaic cells.

EXAMPLE 11

To 15 ml of methanesulfonic acid at 0° C., there is added 5.8 g (10 mmoles) of the potassium salt of 5-perfluorobutanesulfonyl-2-phenyl-2-trifluoromethyl-1,3-dioxolane-4,6-dione, obtained in Example 8, and 3.22 g (10 mmoles) of iodosobenzene diacetate $\phi$—$I(OCOCH_3)_2$ (commercially available from Lancaster). After 6 hours under stirring at 0° C., the reaction mixture was poured into 100 ml of ether, and the precipitate which appeared was recovered by filtration and dried. The zwitterion obtained:

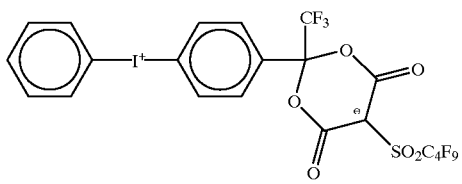

enables to release, under the effect of actinic radiation (light, γ rays, electron beams), an acid which is capable of initiating a polymerization by a cationic mechanism. It is soluble in most of the usual organic solvents (tetrahydrofurane, acetonitrile, dimethyl-formamide, ethyl acetate, glymes, . . . ) and in aprotic solvating polymers such as polyethylene oxide. It is also soluble at more than 5% by weight in reactive solvents such as triethyleneglycol divinyl ether.

EXAMPLE 12

2.8 g (10 mmoles) of 4,4'-azobis(4-cyanovaleric), 3.24 g (20 mmoles) of carbonyldiimidazole and 100 mg of dimethylamino pyridine were suspended in 20 ml of ether and kept at 0° C. When $CO_2$ has ceased to escape (5 hours), there is added 1.44 g (20 mmoles) of the potassium salt of 2,2-trifluoromethyl-1,3-dioxolane-4,6-dione, obtained in Example 8. The mixture was kept under magnetic stirring at 0° C. during 24 hours. By centrifugation, the following crystalline precipitate was isolated:

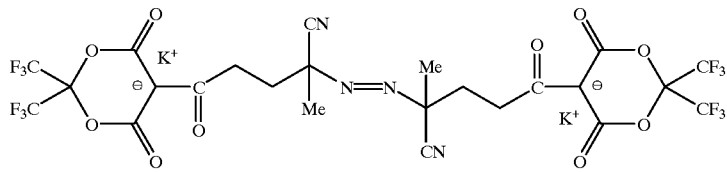

This salt is soluble in most of the usual organic solvents, in particular in acetone, acetonitrile, ethyl acetate, tetrahydrofurane, and in aprotic solvating polymers such as polyethylene oxide. It may be used as a non-volatile free radical initiator to initiate polymerization or cross-linking reactions already at 60° C.

EXAMPLE 13

First, the disodium salt of 2,2'-azinobis(3-ethylbenzothiazoline-6-sulfonic) acid was prepared from its diammonium salt (commercially available from Aldrich) by treating it with a titrated solution of sodium hydroxide. After evaporation and drying, the disodium salt was recovered in quantitative yield. To 1.12 g of the latter (2 mmoles) in 10 ml of anhydrous acetonitrile, there is slowly added 508 mg of oxalyl chloride ClCOCOCl (4 mmoles) in solution in 1 ml of anhydrous dichloromethane. After 4 hours under stirring, 4 ml of anhydrous pyridine and 1.47 g (4 mmoles) of the potassium salt of 1,3-(2,2,2-trifluoroethyl)-2-sulfonyl-barbituric acid, obtained in Example 3, were added. After 24 hours, acetonitrile was evaporated and the residue was reclaimed in 10 ml of water. After adding 1.29 g of tetrabutyl ammonium bromide, the precipitate obtained was extracted with dichloromethane. After drying, the organic phase with magnesium sulfate, evaporation of the solvent and drying, the following compound was obtained:

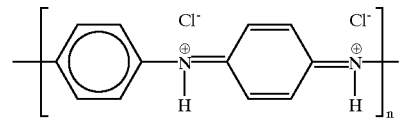

There is then added 9.89 g of the potassium salt of 5-fluoro-1,3-di-2-ethylhexyl-2-sulfonyl-barbituric acid, obtained in Example 6:

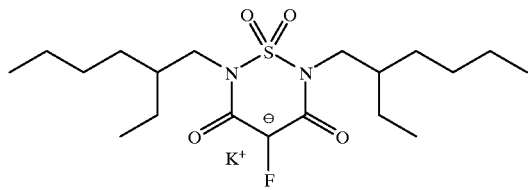

After 48 hours under stirring, a polyaniline doped with 5-fluoro-1,3-di-2-ethylhexyl-2-sulfonyl-barbituric acid, soluble in toluene, was recovered. The doped polyaniline thus obtained is an electronically conductive polymer which has a conductivity, measured by the method of the four points, of 6 S/cm, stable in humid medium.

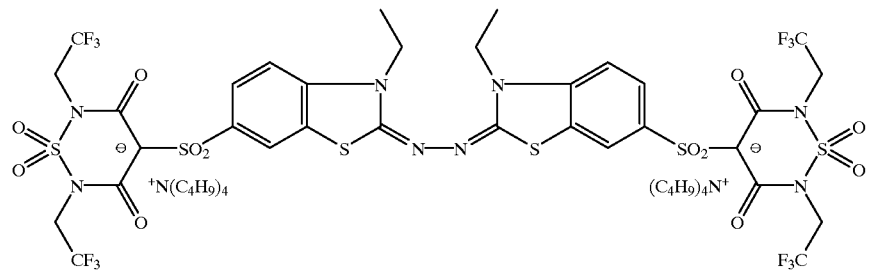

This compound gives by oxidation a radical and a biradical which are stable zwitterions and it enables to produce oxidation catalyses between an oxygenated aqueous phase and an organic phase which is non miscible containing the species to be oxidized.

From a solution in toluene of doped polyaniline, it was possible to produce a film on a polypropylene support (PP) treated by Corona effect. After drying under vacuum at 60° C. during 48 hours, a conductive deposit was obtained which adheres to polyaniline and has a thickness lower than 1 micron. In addition, this electronically conductive polymer is a good corrosion inhibitor for ferrous metals in acid or chloride medium. Treatment of surfaces to be protected is carried out simply by depositing a solution of PCE in the form of a paint, followed by drying and thermal treatment at 100° C.

EXAMPLE 14

2.54 g of polyaniline chloride (AC&T, St Égrève, France) were suspended in 10 ml of water:

EXAMPLE 15

A solution of 17 g (40 mmoles) of the lithium salt of 5-(4-styrenesulfonyl)-2,2-trifluoromethyl-1,3-dioxolane-4,6-dione acid, prepared as in Example 6, 3.18 g of acrylonitrile (60 mmoles) and 100 mg of 1,1'-azobis(cyclohexanecarbonitrile) in solution in 100 ml of anhydrous THF were degassed by flushing with dry argon. Copolymerization of acrylonitrile with the styrene derivative was then carried out under argon at 60° C. during 48 hours. After cooling, the solution was concentrated, and the polymer was recovered by reprecipitation in ether. After filtering and drying, the lithium salt of poly-(acrylonitrile-co-5-(4-styrenesulfonyl)-2,2-trifluoromethyl-1,3-dioxolane-4,6-dione) (PANS2MF) was obtained.

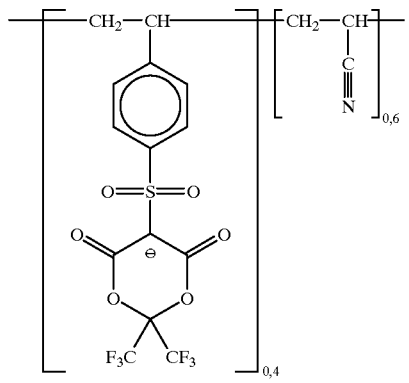

This polymer enables to introduce gelled polymer electrolytes with fixed anions. It constitutes the matrix enabling to obtain the gel and it has the properties of a polyelectrolyte. A gelled electrolyte made of 40% by weight of PANS2MF, 28% by weight of ethylene carbonate, 28% by weight of propylene carbonate and 4% by weight of silica particles (AEROSIL R 974 commercially available from Degussa) was prepared. This gel has good mechanical properties and a conductivity of $5.7 \times 10^{-4}$ S.cm$^{-1}$ at 30° C. The cationic transport number of this electrolyte was estimated to be 0.95.

An electrochemical generator was assembled by utilizing said gelled electrolyte, a composite anode made of a carbon coke (80% by volume) mixed with the copolymer (PANS2MF) as binder (20% by volume), and a composite cathode made of carbon black (6% by volume), LiCoO$_2$ (75% by volume) and some copolymer (PANS2MF) as binder (20% by volume). This generator has enabled to effect 1,000 cycles of charge/discharge between 3 and 4.2 V by maintaining a capacity higher than 80% of the capacity during the first cycle, during a cycling 25° C. It has very good performances during calls for power because of the utilization of fixed anions. The utilization of fixed anions has also enabled to improve the evolution of the interface resistance.

EXAMPLE 16

According to a process similar to one used in Example 15, a copolymer of acrylonitrile (97% molar) and a lithium salt of 5-(4-styrenesulfonyl)-2,2-trifluoromethyl-1,3-dioxolane-4,6-dione acid (3% molar) was synthesized.

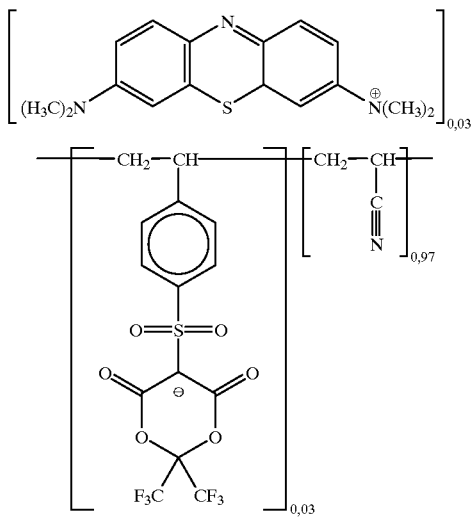

This copolymer, in the form of an alkali metal or ammonium salt, has antistatic properties and may therefore advantageously replace acrylonitrile homopolymers which are to this day largely utilized in the form of fiber for textile, but which has no antistatic properties. Moreover, spinning of this copolymer is easier than that of non-modified PAN.

The copolymer has very good interactions with cationic coloring materials such as methylene blue, which makes it a material of interest for colored textile fibers. The stability of the color being clearly improved with respect to the known copolymer of acrylonitrile and methallylsulfonate.

EXAMPLE 17

To 4.9 g of the sodium salt of Nickel (II) phthalocyanine-tetrasulfonic acid (5 mmoles), commercially available from Aldrich) in 40 ml of anhydrous dimethylformamide (DMF), there is added by portions 3.2 g of (chloromethylene) dimethylammonium chloride [(CH$_3$)$_2$N=CHCl]$^+$,Cl$^-$ (25 mmoles, commercially available from Aldrich). After 4 hours under stirring, the reaction mixture was centrifuged, the floating liquid was removed and the decanted product was reclaimed in 40 ml of anhydrous DMH. There is then added 2 ml of pyridine and 7.81 g (20 mmoles) of the potassium salt 1-(2,2,3,3,3-pentafluoropropyl)-3-butyl-2-sulfonyl-barbituric acid obtained in Example 5. After 48 hours under stirring, the reaction mixture was stirred 24 hours with 2 g of potassium carbonate Li$_2$CO$_3$. After evaporation of DMF and drying, the following compound was obtained:

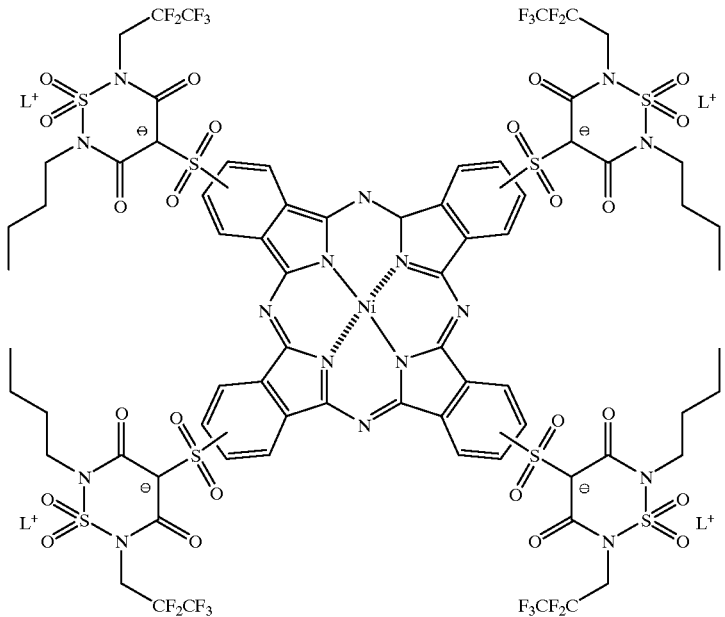

which is soluble in most of the usual organic solvents (tetrahydrofurane, acetonitrile, dimethylformamide, ethyl acetate, glymes, . . . ) and in polar polymers. It has an important absorption in visible range. In the form of tetrabutylammonium tetrasalt, it is also soluble in low polar solvents such as dichloromethane or methylene chloride as well as in low polar polymer matrices such as methyl polymethacrylate.

Grafting of 1-(2,2,3,3,3-pentafluoropropyl)-3-butyl-2-sulfonyl-barbituric acid also enables to clearly decrease the aggregation of the molecules of this cationic coloring materials between one another, which phenomenon of aggregation brings about a widening of the optical absorption bands which is prejudicial to the preciseness of the systems utilizing its coloring materials in particular optical disk for storing information.

EXAMPLE 18

To 3.2 g (25 mmoles) of 2-(3-thienyl)ethanol in 60 ml of anhydrous dimethylformamide, there is added 8.4 g (25 mmoles) of the potassium salt of 2 -methyl-2-heptafluoropropyl-1,3-dioxolane-4,6-dione, obtained in Example 8, 3.46 g of anhydrous potassium carbonate $K_2CO_3$ and 330 mg (1.25 mmoles) of a crown ether, 18-Crown-6 (acting as complexent of the potassium cation). The reaction mixture was then stirred under argon at 85° C. After 48 hours, the reaction mixture was filtered on a fritted glass of porosity N° 3, and the solvent was evaporated under reduced pressure. After drying, the compound was recrystallized in 20 ml of water containing 1.86 g (25 mmoles) of anhydrous potassium chloride KCl. After filtering and drying, the following compound was recovered:

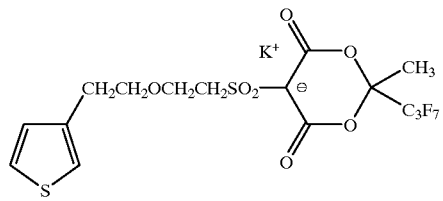

10 ml of a $5 \times 10^{-2}$ of said compound in acetonitrile were prepared and an electropolymerization was carried out in the anodic compartment of an electrochemical cell on a platinum electrode. A flexible conductor film was obtained:

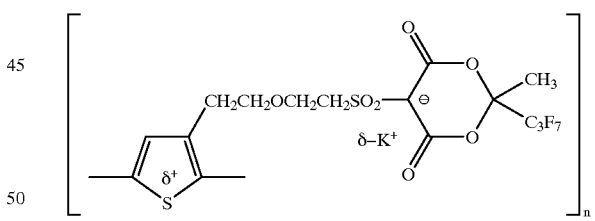

in which the doping (oxidation) is ensured by exchange of cations and electrons with the outside. The conductivity of this material is of the order of 10 $S.cm^{-1}$ and it is stable at room temperature and in humid medium. The electropolymerization carried out in the presence of non-substituted pyrrol or having oxyethylene chains in position N or 3 gives polymers which are also stable and in which the change of colour may be used to constitute electrochrome systems.

EXAMPLE 19

To 400 mg (1 mmole) of 1-(2,2,3,3,4,4,4-heptafluorobutyl)-3-butyl-2-sulfonyl-barbituric acid, obtained in Example 5, in 5 ml of water under stirring, there are added 2 drops of concentrated sulfuric acid. After 4 hours under stirring, 60 mg of anhydrous lithium carbonate Li$_2$CO$_3$ were added, and after 15 min 322 mg (1 mmole) of tetrabutylammonium (C$_4$H$_9$)$_4$NBr. By extraction with dichloromethane, the following compound was recovered:

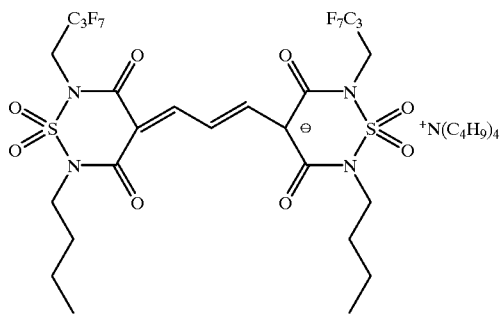

This anionic absorbing coloring material in the visible range is soluble in low polar solvents such as dichloromethane or methylene chloride as well as in low polar polymer matrices such as methyl polymethacrylate. The low degree of aggregation of the molecules of this anionic colouring material with one another prevents the phenomenon of widening of the optical absorption bands of this colouring material.

EXAMPLE 20

In a three neck flask provided with a cooler, a mechanical stirrer and a neutral gas inlet (Argon), there is introduced 9.5 g of a copolymer of dimethylsiloxane and (hydrogeno)(methyl)-siloxane (HMS 301 25% SiH, M$_w$ 1900, commercially available from Gelest Inc., Tullytown, Pa., USA) in solution in tetrahydrofurane. 14.03 g of the lithium salt of 5-trifluoro-acetyl-3-allyl-1-butyl-barbituric, obtained in Example 1, and 70 mg of chloroplatinic acid H$_2$PtCl$_6$ were then added. The mixture was heated to reflux during 4 hours. The polymer was then reprecipitated in ether, redissolved in THF and again reprecipitated in ether. The following polymer was obtained:

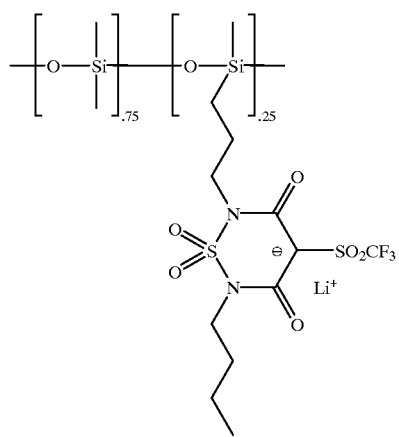

which is soluble in most of the organic solvents, including at contents >2% in oils or silicon materials, to which it gives antistatic properties.

EXAMPLE 21

In a Parr chemical reactor, 12.9 g (50 mmoles) of the lithium salt of 2,2-trifluoro-methyl-1,3-dioxolane-4,6-dione, obtained in Example 8, and 176 mg of a crown ether, the 12-Crown-4 (acting as a complexent of the lithium cation) were solubilized in 60 ml of anhydrous acetonitrile. After closing the reactor, flushing with argon during 15 min was carried out before isolating it. There are then introduced, 6.41 g (50 mmoles) of sulfur dioxide SO$_2$ (commercially available from Fluka), and, after 10 min, 9.52 g (50 mmoles) of vinyltriethoxysilane (commercially available from Fluka) in solution in 20 ml of anhydrous acetonitrile. After 6 hours at room temperature, the reactor was heated to 40° C. and kept at that temperature during 48 hours, and the solvent was evaporated. After drying under vacuum, the following compound was obtained in quantitative yield:

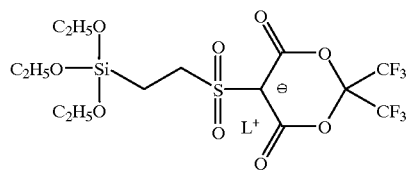

This salt may constitute organosilicon networks by a mechanism of hydrolysis-polycondensation. It may also be used with glass based materials (fiber,glazing, . . . ) in order to modify their surface and in particular to give them antistatic properties. A solution of this salt with O—[2-(trimethoxysilyl)-ethyl]—O'—methylpolyethylene glycol of molecular weight 5,000 (commerically available from Shearwaters Polymers) (3:1 molar) was prepared in a water/methanol mixture. A glass plate cleaned with nitric acid and dried at 100° C. was then soaked in the solution during a few minutes. After rinsing with methanol and drying, a surface conductivity of 3×10$^{-5}$S(square) sufficient to give antistatic and hydrophilic properties to the glass surface was measured.

EXAMPLE 22

5.97 g (10 mmoles) of the potassium salt of 5-perfluorobutanesulfonyl-1,3-dibutyl-2-sulfonyl-barbituric acid, prepared according to Example 5, and 3.17 g (10 mmoles) of diphenyliodonium (C$_6$H$_5$)$_2$ICl were stirred together during 24 hours in water. By extraction of the aqueous phase with dichloromethane, the following compound was recovered:

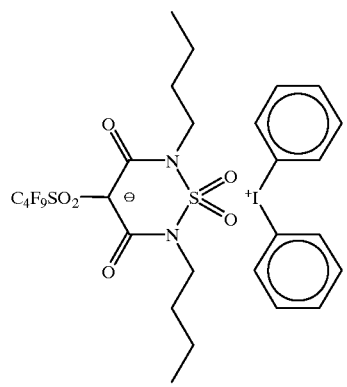

This salt is particularly active as cationic polymerization photoinitiator, in particular for divinylethers such as triethylene glycol divinylether (DVE-3). This initiator has a solubility and an activity higher than that of the same sulfonium salt associated with PF$_6^-$ or SbF$_6^-$.

EXAMPLE 23

2.22 g (5 mmoles) of tetrakis(acetonitrile)palladium (II) tetrafluoroborate $(CH_3CN)_4Pd(BF_4)_2$ (commercially available from Aldrich), in 30 ml of tetrahydrofurane, were treated with 5.97 g (10 mmoles) of the potassium salt of 5-perfluorobutanesulfonyl-1,3-dibutyl-2-sulfonyl-barbituric acid obtained in Example 2. After 24 hours under stirring, the reaction mixture was filtered to remove the precipitate of potassium tetrafluoroborate $KBF_4$, and the solvent was evaporated. The following compound was obtained in quantitative yield:

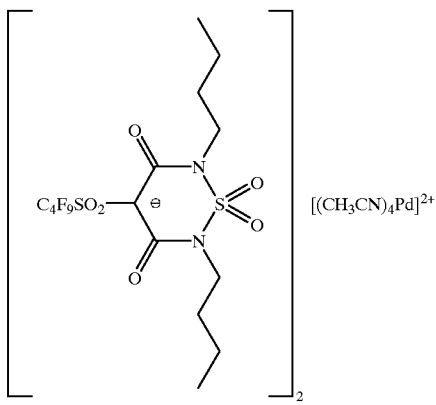

This salt is a catalyst for the vinyl polymerization of norbornene even in low polar solvents such as dichloromethane.

EXAMPLE 24

During a first step, ferrocene dilithium complexed with tetramethylethylenediamine (TMEDA) was prepared: In a glove box under argon, there is added 37 ml of freshly distilled TMEDA (247 mmoles) and 40 ml of anhydrous hexane in a 1 l flask. There is then added drop wise 154 ml of a 1.6 M solution of butyllithium in hexane (247 mmoles, commercially available from Aldrich). After 10 min, there is added drop wise 18.6 g of ferrocene (100 mmoles) in solution in 500 ml of anhydrous hexane while keeping a strong stirring of the solution. After one night, orange crystals appeared in the solution, which were recovered by filtering the solution on a fritted glass of porosity N° 4. After drying under vacuum, there is obtained 28.4 g of 1,1'-dilithio-ferrocene●2 TMEDA (66% yield) which was preserved under argon.

8.61 g (20 mmoles) of this compound in 30 ml of anhydrous acetonitrile were then treated with 4.89 g of 1,3-propane sultone (40 mmoles) in a glove box. After 24 hours at room temperature, 2 drops of dimethylformamide were added in the reaction mixture, and there is slowly added 5.08 g of oxalyl chloride ClCOCOCl (40 mmoles) in solution in 15 ml of anhydrous dichloromethane. After 4 hours at room temperature, 5 ml of pyridine and 11.61 g (40 mmoles) of the potassium salt of 2,2-trifluoromethyl-1,3-dioxolane-4,6-dione prepared as in Example 8 were added. The reaction was continued during 24 hours, and the reaction mixture was stirred 24 hours in the presence of 4 g of lithium carbonate $Li_2CO_3$. After filtering and evaporation of the solvents, and drying, the following compound was recovered:

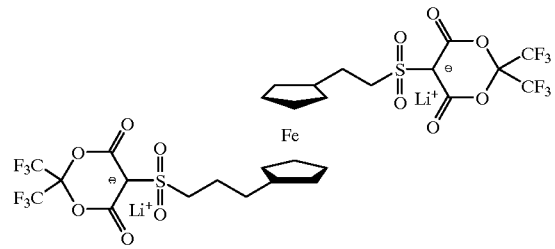

This salt is soluble in most of the usual organic solvents (tetrahydrofurane, acetonitrile, dimethylformamide, ethyl acetate, glymes, . . . ) and in polar polymers.

It has a reversible redox couple. In polyethylene oxide, it was possible to determine, on a platinum electrode of a diameter 125 $\mu$m, a reversible potential of 3.4 V towards a lithium electrode.

When dissolved in a liquid, gel or polymer electrolyte, it enables to provide a protection in overcharge thereby acting as a redox shuttle. It also enables to provide electrochrome systems with colouring materials.

EXAMPLE 25

Catalysis of an Aldol Condensation

The scandium salt of 5-trifluoromethanesulfonyl-1,3-dubutyl-2-sulfonyl-barbituric acid was obtained by treating the potassium salt, obtained in Example 2, with a stoichiometric quantity of scandium tetrafluoroborate $Sc(BF_4)_3$ in acetonitrile. After filtering to eliminate the precipitate of potassium tetrafluoroborate $KBF_4$ and evaporation of the solvent, the scandium salt of dibutylaminosulfonylmalononitrile $(Sc(DBTFSB)_3)$ was recovered in quantitative yield.

The catalytic effect of this salt in an aldol condensation was evaluated in the following manner. To a solution containing 507 mg (0.4 mmoles) of the scandium salt of 5-trifluoromethylsulfonyl-1,3-dibutyl-2-sulfonyl-barbituric acid (10% molar) in 15 ml of dichloromethane, there is added a mixture of 1.05 g (6 mmoles) of 1-ene-2-methyl-1-silylacetal-1-methoxypropene $(CH_3)_2C=C(OSiMe_3)$ OMe and 420 mg (4 mmoles) of benzaldehyde in 10 ml of dichloromethane. After 16 hours under stirring at room temperature, water was added and the product was extracted with dichloromethane. the organic phase was washed with three fractions of 100 ml of water and dichloromethane was evaporated. The residue was then treated with a tetrahydrofurane/HCl 1 M (20:1) mixture during 0.5 hours at 0° C. After diluting with hexane, a saturated solution of sodium bicarbonate was added, and the product was extracted with dichloromethane. The organic phase was washed with a saturated solution of sodium chloride, and dried with sodium sulfate. After evaporation of the solvents, the raw product was chromatographed on silica gel. Methyl-3-hydroxy-2,2-dimethyl-phenylpropionate was obtained with a yield of 91% in accordance with the results obtained with the ytterbium triflate salt of the prior art.

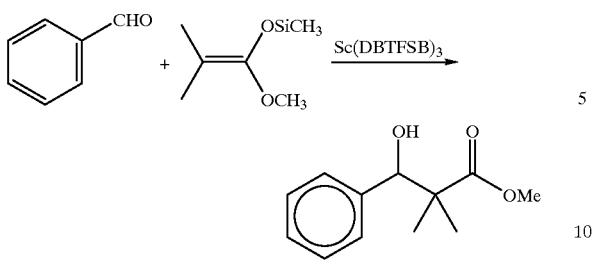

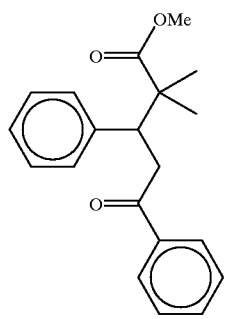

The same reaction was carried out with a decreased quantity of catalyst by a factor near five, without decreasing the yield of the compound methyl- 3-hydroxy-2,2-dimethyl-phenylprionate. This result is due to the better solubility in dichloromethane of the scandium salt of 5-trifluoromethanesulfonyl-1,3-dibutyl-2-sulfonyl-barbituric acid, as compared to the ytterbium triflate salt, used in the prior art.

EXAMPLE 26

Catalysis of an Addition of Michael

The catalytic effect of the scandium salt of 5-trifluoromethanesulfonyl-1,3-dibutyl-2-sulfonyl-barbituric acid, obtained in Example 25, towards a Michael addition was evaluated in the following manner. To a solution of 507 mg (0.4 mmoles) of the scandium salt of dibutylaminosulfonylmalononitrile (10% molar) in 10 ml of dichloromethane, there is added a mixture of 840 mg (4 mmoles) of chalcone and 1.05 g (6 mmoles) of 1-ene-2-methyl-1-silylacetal-1-methoxypropene $(CH_3)_2C=C(OSiMe_3)OMe$ in 10 ml of dichloromethane. After 12 hours under stirring at room temperature, water is added and the product was extracted with dichloromethane. The organic phase was is washed with three fractions of 100 ml water, and dichloromethane was evaporated. The residue was then treated with a tetrahydrofurane/HCl 1 M (20:1) mixture during 0.5 hours at 0° C. After diluting with hexane, a saturated solution of sodium bicarbonate was added, and the product was extracted with dichloromethane. The organic phase was washed with a saturated solution of sodium chloride, and dried with sodium sulfate. After evaporation of the solvents, the raw product was chromatographed on a silica gel. The 1,5-dicarbonylated compound was obtained with a yield of 85% in accordance with the results obtained with the ytterbium triflate salt of the prior art.

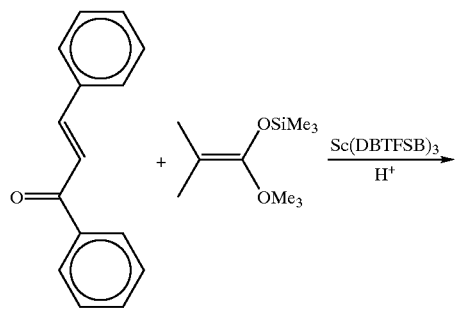

The same reaction was carried out with a decreased quantity of catalyst by a factor near five, without decreasing the yield in the 1,5-dicarbonylated compound. This result is due to the better solubility in the dichloromethane of the scandium salt of 5-trifluoromethanesulfonyl-1,3-dibutyl-2-sulfonylbarbituric acid, as compared to the ytterbium triflate salt.

EXAMPLE 27

Catalysis of a Friedel-Crafts Acylation Reaction

The catalytic effect of the scandium salt of 5-trifluoromethanesulfonyl-1,3-dibutyl-2-sulfonyl-barbituric acid, obtained in Example 25, towards a Friedel-Crafts reaction of acylation was evaluated in the following manner. In 40 ml of anhydrous nitromethane, there is added 887 mg (0.7 moles) of the scandium salt of 5-trifluoromethylsulfonyl-1,3-dibutyl-2-sulfonyl-barbituric acid, and 1.08 g (10 mmoles) of anisole and 2.04 g (20 mmoles) of acetic anhydride. After stirring during 10 min at 21° C., the reaction mixture was diluted with 50 ml of ether and the reaction was inhibited with 100 ml of a saturated solution of sodium bicarbonate $NaHCO_3$. After filtration on Celite, the solution was extracted with three fractions of 50 ml ether, then the collected ether phase was washed with a saturated solution of potassium chloride. After drying the ether phase with magnesium sulfate and evaporation, 1.46 g of p-methoxyacetophenone (95% yield) were recovered with a purity characterized by a proton RMN higher than 99%.

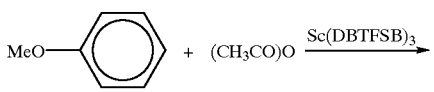

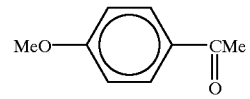

EXAMPLE 28

The catalytic effect of the scadium salt of 5-trifluoromethanesulfonyl-1,3-dibutyl-2-sulfonyl-barbituric acid, obtained in Example 25, towards a Diels-Alder reaction, was evaluated by carrying out the following reaction.

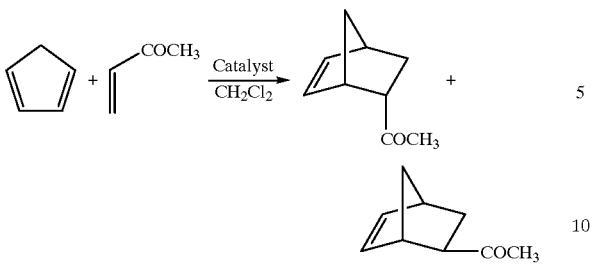

To a solution of 651 of freshly distilled cyclopentadiene (10 mmoles) and 701 mg of methylvinylketone in 10 ml of dichloromethane, there is added 200 μmoles of the scandium salt of 5-trifluoromethylsulfonyl-1,3-dibutyl-2-sulfonyl-barbituric acid. After 24 hours at room temperature, the reaction mixture was filtered to remove the catalyst in suspension. There is obtained a reaction yield, determined by chromatography in gaseous phase, higher than 90%.

EXAMPLE 29

The lithium salt of 5-trifluoromethyl-sulfonyl-1,3-dibutyl-2-sulfonyl-barbituric acid, obtained in Example 2, and the lithium salt of 5-cyano-2,2-trifluoromethyl-1,3-dioxolane-4,6-dione acid, obtained in Example 8, were tested in electrochemical generators of lithium-polymer technology.

For each salt, a battery was prepared by superposing the following layers:
- a stainless steel current collector with a thickness of 2 mm;
- a cathode consisting of a pastil of a film of composite material having a thickness of 89 μm an consisting of vanadium dioxide (45% by volume), Shawinigan black (5% by volume) and polyethylene oxide of molecular weight $M_W = 3 \times 10^5$ (50% by volume);
- an electrolyte consisting of a pastil of a film of polyethylene oxide of molecular weight $M_W = 5 \times 10^6$ containing one of the two lithium salts at a concentration O/Li= 15/1;
- an anode consisting of a sheet of metallic lithium having a thickness of 50 μm;
- a current collector similar to the above current collector.

The pastils constituting the electrodes and the electrolyte were cut in a glove box and piled in the order indicated above. The collectors were then placed on both sides of the pile obtained.

The assembly was sealed in a button shaped battery housing which enables simultaneously to protect the generator from the atmosphere and to exert a mechanical stress on the films. The battery was then placed in an enclosure under argon mounted in a drying oven at a temperature of 60° C. It was then cycled between 1.8 and 3.3 V at a rate of charge and discharge C/10 (nominal capacity charge or discharge in 10 hours).

The curve of cycling obtained by utilizing the lithium salt of 5-trifluoromethylsulfonyl-1,3-dibutyl-2-sulfonyl-barbituric acid is given in FIG. 1. In this figure, the utilization, U, expressed in % is given in ordinate, and the number of cycles, C, is given in abscissae.

Similar cycling result is obtained with the lithium salt of 5-cyano-2,2-trifluoromethyl-1,3-dioxolane-4,6-dione acid.

What is claimed is:

1. Ionic compound comprising at least one anionic part associated to at least one cationic part M in sufficient number to ensure an electronic neutrality to the compound, characterized in that M is a hydroxonium, a nitrosonium $NO^+$, an ammonium $—NH_4^+$, a metallic cation having a valence m, an organic cation having a valence m or an organometallic cation having a valence m, and in that the anionic part is an aromatic heterocycle corresponding to the formula (A)

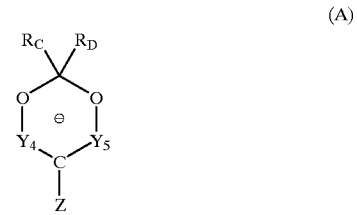

in which:
- $Y_4$ and $Y_5$ represent independently from one another a carbonyl group, a sulfonyl group, a thiocarbonyl group, a thionyl group, a —C(=NCN)— group or a —C(=C(CN)$_2$)— group;
- Z represents an electroattractor radical having a Hammett parameter at least equal to that of a fluorine atom;
- each of the substituents $R_C$ and $R_D$ represent independently from one another a monovalent or divalent organic radical, or is part of a polymer chain, at least one of the substitutents $R_C$ and $R_D$ being a perfluorinated radical.

2. A compound according to claim 1, characterized in that the organic cation is selected from a group consisting of cations $R_3O^+$ (oxonium), $NR_4^+$ (ammonium), $RC(NHR_2)_2^+$ (amidinium), $C(NHR_2)_3^+$ (guanidinium), $C_5R_6N^+$ (pyridinium), $C_3R_5N_2^+$ (imidazolium), $C_3R_7N_2^+$ (imidazolinium), $C_2R_4N_3^+$ (triazolium), $SR_3^+$ (sulfonium), $PR_4^+$ (phosphonium), $IR_2^+$ (iodonium), $(C_6R_5)_3C^+$ (carbonium), the radicals R independently representing an H or a radical selected from the group consisting of:
- alkyl, alkenyl, oxa-alkyl, oxa-alkenyl, aza-alkyl, aza-alkenyl, thia-alkyl, thia-alkenyl, sila-alkyl, sila-alkenyl, aryl, arylalkyl, alkylaryl, alkenylaryl, dialkylamino and dialkylazo radicals;
- cyclic or heterocyclic radicals optionally comprising at least one lateral chain comprising heteroatoms such as nitrogen, oxygen, sulfur;
- cyclic or heterocyclic radicals optionally comprising heteroatoms in the aromatic nucleus;
- groups comprising a plurality of aromatic or heterocyclic nuclei, condensed or non-condensed, optionally containing at least one nitrogen, oxygen, sulfur or phosphorus atom;
- with the proviso that a plurality of radicals R may together form aliphatic or aromatic cycles optionally enclosing the center carrying the cationic charge.

3. Compound according to claim 2, characterized in that the oxonium, ammonium, sulfonium, phosphonium, iodonium or carbonium cation is part of the radical Z.

4. Compound according to claim 2, characterized in that the oxonium, ammonium, sulfonium, phosphonium, iodonium or carbonium cation is part of a recurring unit of a polymer.

5. Compound according to claim 2, characterized in that the oxonium, ammonium, sulfonium, phosphonium, iodonium or carbonium cation comprises a cationic heterocyclic group with aromatic character, including at least one alkylated nitrogen atom in the cycle.

6. Compound according to claim 5, characterized in that the oxonium, ammonium, sulfonium, phosphonium, iodonium or carbonium cation comprises an imidazolium group, a triazolium group, a pyridinium group, a 4-dimethylaminopyridinium group, said groups optionally carrying a substituent on the carbon atoms of the cycle.

7. Compound according to claim 2, characterized in that the oxonium, ammonium, sulfonium, phosphonium, iodonium or carbonium cation comprises a group having a bond —N=N—, —N=N$^+$, a sulfonium group, an iodonium group, or a substituted or non-substituted arene-ferrocenium cation, possibly incorporated in a polymeric network.

8. Compound according to claim 2, characterized in that the oxonium, ammonium, sulfonium, phosphonium, iodonium or carbonium cation is a diaryliodonium cation, a dialkylaryliodonium cation, a triarylsulfonium cation, a trialkylaryl sulfonium cation, or a substituted or non-substituted phenacyl-dialkyl sulfonium cation.

9. Compound according to claim 2, characterized in that the cation is part of a polymer chain.

10. Compound according to claim 2, characterized in that the oxonium, ammonium, sulfonium, phosphonium, iodonium or carbonium cation comprises a group 2,2'[azobis(2-2'-imidazolinio-2-yl)propane]$^{2+}$ or 2,2'-azobis(2-amidiniopropane)$^{2+}$.

11. Compound according to claim 1 characterized in that the cation M is a metallic cation selected from the group consisting of cations of alkali metals, cations of alkali earth metals, cations of transition metals, cations of trivalent metals, cations of rare earths and organometallic cations.

12. Compound according to claim 1, characterized in that the cation is a metallocenium, selected from the group consisting of cations derived from ferrocene, titanocene, zirconocene, indenocenium cations, arene metallocenium cations, cations of transition metals complexed with ligands of phosphine type possibly having a chirality and organometallic cations having one or more alkyl or aryl groups covalently fixed to an atom or a group of atoms, said cations possibly being part of a polymeric chain.

13. Compound according to claim 1, characterized in that one of the substituents $R_C$ and $R_D$ represents:
 a) an alkyl, an alkenyl, an oxa-alkyl, an oxa-alkenyl, an aza-alkyl, an aza-alkenyl, a thia-alkyl, a thia-alkenyl, said radicals possibly carrying at least one aryl group;
 b) an aryl carrying optionally least one radical as defined in a);
 c) an alicyclic radical or an aromatic radical optionally carrying at least one lateral chain comprising a heteroatom or optionally comprising at least one heteroatom in the cycle;
 d) a radical as defined above in a), b) and c) and additionally carrying halogen atoms, in halogenated or perhalogenated form.

14. Compound according to claim 13, characterized in that one of the substituents $R_C$ and $R_D$ is selected from alkyl radicals and alkenyl radicals having 1 to 10 carbon atoms.

15. Compound according to claim 13, characterized in that one of the substituents $R_C$ and $R_D$ is selected from alkyl or halogenated or perhalogenated alkenyl radicals having 1 to 10 carbon atoms.

16. Compound according to claim 13, characterized in that one of the substituents $R_C$ and $R_D$ is selected from oxa-alkyl or oxa-alkenyl radicals having 1 to 10 carbon atoms.

17. Compound according to claim 1, characterized in that Z is a $R_E Y_E$— radical or a $R_E Y_G PO$— radical in which $Y_E$ represents a carbonyl group, a sulfonyl group or a thionyl group, and $R_E$ and $R_G$ represent independently from one another a halogen or an organic radical.

18. Compound according to claim 17, characterized in that Z is a radical $R_E SO_2$—.

19. Compound according to claim 17, characterized in that $R_E$ and $R_G$ represent independently from one another an alkyl, alkenyl, oxa-alkyl, oxa-alkenyl, aza-alkyl, aza-alkenyl, thia-alkyl, thia-alkenyl, aryl, alkylaryl, alkenylaryl, arylalkyl, arylalkenyl radical, an alicyclic radical or an aromatic radical optionally carrying at least one lateral chain comprising a heteroatom or optionally comprising at least one hetero atom in the cycle, said $R_E$ and $R_G$ possibly being halogenated or perhalogenated.

20. Compound according to claim 17, characterized in that $R_E$ and $R_G$ are selected independently from alkyl or alkenyl radicals having 1 to 12 carbon atoms and optionally comprising at least one heteroatom O, N or S in the main chain or in a lateral chain, and carrying a hydroxy group, a carbonyl group, an amine group, a carboxyl group.

21. Compound according to claim 17, characterized in that $R_E$ and $R_G$, are selected independently from one another from aryl, arylalkyl, alkylaryl or alkenylaryl radicals, in which the aromatic nuclei, condensed, comprise heteroatoms such as nitrogen, oxygen, sulfur.

22. Compound according to claim 17, characterized in $R_E$ or $R_G$ is a radical having an iodonium, a sulfonium, oxonium, ammonium, amidinium, guanidinium, guanidinium, pyridinium, imidazolium, triazolium, phosphonium or carbonium group, said ionic group behaving totally or partially as cation M.

23. Compound according to claim 17, characterized in that $R_E$ or $R_G$ includes at least one ethylenic unsaturation and/or a condensable group and/or a group which is thermally, photochemically or ionically dissociable.

24. Compound according to claim 17, characterized in that $R_E$ or $R_G$ represents a mesomorphous group or a chromophore group or a self-doped electronically conductive polymer or a hydrolyzable alkoxysilane.

25. Compound according to claim 17, characterized in that $R_E$ or $R_G$ includes a group capable of trapping free radicals.

26. Compound according to claim 17, characterized in that $R_E$ or $R_G$ includes a dissociating dipole.

27. Compound according to claim 17, characterized in that $R_E$ or $R_G$ includes a redox couple.

28. Compound according to claim 17, characterized in that $R_E$ or $R_G$ includes a complexing ligand.

29. Compound according to claim 17, characterized in that $R_E$—$Y_E$— or $R_E R_G PO$ is optically active.

30. Compound according to claim 17, characterized in that $R_E$—$Y_E$— represents an amino acid, or an optically or biologically active polypeptide.

31. Compound according to claim 1, characterized in that Z is selected from a group consisting of —F, —Cl, —Br, —CN, —$NO_2$, —SCN and —$N_3$—.

32. Compound according to claim 1, characterized in that Z is selected from the radicals —$C_n F_{2n+1}$, —O—$C_n F_{2n+1}$, —S—$C_n F_{2n+1}$, —$CH_2$—$C_n F_{2n+1}$, —O—CF=$CF_2$ or —SCF=$CF_2$, $1 \leq n \leq 8$.

33. Compound according to claim 1, characterized in that Z comprises a heterocycle derived from fluorinated or non-fluorinated pyridine, pyrazine, pyrimidine, oxadiazole or thiadiazole.

34. Compound according to claim 1, characterized in that Z is a radical having a valency v at least equal to 2 and connecting v ionic groups

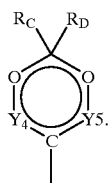

35. Compound according to claim 33, characterized in that radical Z is a bivalent radical comprising at least one —$SO_2$— group, one —CO— group, a perfluoroalkylene group having 2 to 8 carbon atoms, a phenylene group optionally substituted with heteroatoms, a group —(W=W)$_n$— or a cationic group —(W=W)$_n$—$W^+$—, in which W represents a nitrogen atom or a —C(R)—, R representing a hydrogen atom or an organic radical having 1 to 8 carbon atoms, or two radicals R carried by adjacent carbon atoms forming a cycle, and 0<n<5.

36. Compound according to claim 1, in which Z is part of a recurring unit of a polymer chain.

37. Compound according to claim 17, characterized in that $R_E$ or $R_G$ is part of a poly(oxyalkylene) radical or of a polystyrene radical.

38. Ionically conductive material comprising an ionic compound in solution in a solvent, characterized in that the ionic compound is a compound according to claim 1.

39. Ionically conductive material according to claim 38, characterized in that the cation of the ionic compound is ammonium, a cation derived from a metal, or an organic cation substituted by ammonium, imidazolium, triazolium, pyridinium or 4-dimethylamino-pyridinium, said organic cations optionally carrying a substituent on the carbon atoms of the cycle.

40. Ionically conductive material according to claim 38, characterized in that the ionic compound is such that at least one of the substituents $R_C$, $R_D$, $R_E$, or $R_G$ is an alkyl group, an aryl group, an alkylaryl group or an arylalkyl group, or an alkyl or alkenyl group which contains at least one heteroatom selected from O, N and S and/or an hydroxy group, a carbonyl group, an amino group, a carboxyl group.

41. Ionically conductive material according to claim 38, characterized in that at least one of the substituents $R_E$ or $R_G$ is selected from aryl, arylalkyl, alkylaryl or alkenylaryl radicals, in which the lateral chains and/or the aromatic nuclei comprise heteroatoms such as nitrogen, oxygen, sulfur.

42. Ionically conductive material according to claim 38, characterized in that the substituent Z is selected from the group consisting of —$OC_nF_{2n+1}$, —$OC_2F_4H$, —$SC_nF_{2n+1}$, —$SC_2F_4H$, —$OCF=CF_2$, —$SCF=CF_2$, n being a whole number from 1 to 8.

43. Ionically conductive material according to claim 38, characterized in that the substituent Z represents a recurring unit of a polymer.

44. Ionically conductive material according to claim 38, characterized in that the solvent is either an aprotic liquid solvent selected from linear ethers and cyclic ethers, esters, nitriles, nitro derivatives, amides, sulfones, sulfolanes, sulfamides and partially halogenated hydrocarbons, or a polar polymer, or a mixture thereof.

45. Ionically conductive material according to claim 44, characterized in that the solvent is a solvating polymer, cross-linked or non-cross-linked, which may carry grafted ionic groups.

46. Ionically conductive material according to claim 45, characterized in that the solvating polymer is selected from polyethers of linear structure, comb or blocks, which may form a network based on poly(ethylene oxide), copolymers containing ethylene oxide or propylene oxide or allylglycidylether units, polyphosphazenes, cross-linked networks based on polyethylene glycol cross-linked with isocyanates, networks obtained by polycondensation and carrying groups which enable the incorporation of cross-linkable groups and block copolymers in which certain blocks carry functions with redox properties.

47. Ionically conductive material according to claim 38, characterized in that the solvent consists essentially of an aprotic liquid solvent and a polar polymer solvent comprising units containing at least one heteroatom selected from sulfur, oxygen, nitrogen and fluorine.

48. Ionically conductive material according to claim 47, characterized in that the polar polymer cation mainly contains units derived from acrylonitrile, vinylidene fluoride, N-vinylpyrrolidone or methyl methacrylate.

49. Ionically conductive material according to claim 38, characterized in that it additionally contains at least a second salt and/or a mineral or organic charge in the form of powder of fibers.

50. Electrochemical generator comprising a negative electrode and a positive electrode separated by an electrolyte, characterized in that the electrolyte is a material according to one of claims 38 to 49.

51. Generator according to claim 50, characterized in that the negative electrode consists of metallic lithium, or an alloy thereof, possibly in the form of nanometric dispersion in lithium oxide, or a double nitride of lithium and a transition metal, or an oxide with low potential having the general formula $Li_{1+y+x/3}Ti_{2-x/3}O_4$ ($0 \leq x \leq 1$, $0 \leq y \leq 1$), or carbon and carbonated products produced by pyrolysis of organic material.

52. Generator according to claim 50, characterized in that the positive electrode is selected from vanadium oxides $VO_x$ ($2 \leq x \leq 2,5$), $LiV_3O_8$, $Li_yNi_{1-x}Co_xO_2$, ($0 \leq x \leq 1$; $0 \leq y \leq 1$), spinels of manganese $Li_yMn_{1-x}M_xO_2$ (M=Cr, Al, V, Ni, $0 \leq x \leq 0,5$; $0 \leq y \leq 2$), organic polydisulfides, FeS, $FeS_2$, iron sulfate $Fe_2(SO_4)_3$, phosphates and phosphosilicates of iron and lithium of olivine structure, or substituted products wherein iron is replaced by manganese, used alone or in mixtures.

53. Generator according to claim 50, characterized in that the collector of the cathode is made of aluminum.

54. A process of using an ionic material as an electrolyte, said process comprising contacting at least one carbon electrode with high specific surface, or at least one electrode containing a redox polymer, with an electrolyte material, in which the electrolyte is a material according to one of claims 38 to 49.

55. A process of using a material according to one of claims 38–49 for doping a p or n polymer with electronic conduction, said process comprising contacting a p or n polymer with said material.

56. Electrochrome device, in which the electrolyte is a material according to one of claims 38 to 49.

57. Process of polymerization or cross-linking of monomers or prepolymers capable of cationic reaction, said process comprising utilizing a compound according to claim 1 as photoinitiator constituting a source of acid catalyzing the reaction.

58. Process according to claim 57, characterized in that there is used an ionic compound in which the cation is a group having a bond —N=$N^+$, —N=N— a sulfonium group, an iodonium group, or an arene-ferrocenium cation which is substituted or non-substituted, optionally incorporated in a polymeric network.

59. Process according to claim 57, characterized in that the monomers are selected from the group consisting of compounds which include a cyclic ether function, a cyclic thioether function or a cyclic amine function, vinyl compounds, vinylethers, oxazolines, lactones and lactames.

60. Process according to claim 57, characterized in that the prepolymer is selected from the group consisting of compounds in which epoxy groups are carried by an aliphatic chain, an aromatic chain, or a heterocyclic chain.

61. Process according to claim 57, characterized in that it consists in mixing the photoinitiator with at least one monomer or prepolymer capable of cationic polymerization, and subjecting the mixture obtained to actinic radiation, including β radiation.

62. Process according to claim 57, characterized in that the reaction mixture is subjected to radiation after having been formed into a thin layer.

63. Process according to claim 57, characterized in that the photoinitiator is used in the form of a solution in a solvent which is inert towards the polymerization reaction.

64. Process according to claim 63, characterized in that the inert solvent is selected from the group consisting of acetone, methyl-ethyl ketone, acetonitrile, propylene carbonate, γ-butyrolactone, ether-esters of mono-, di-, tri-ethylene or propylene glycols, ether-alcohols of mono-, di-, tri-ethylene or propylene glycols, esters of phthalic acid or citric acid.

65. Process according to claim 57, characterized in that the reaction is carried out in the presence of a solvent or a diluent consisting of a compound which is reactive towards polymerization.

66. Process according to claim 57, characterized in that the reactive compound is selected from the group consisting of mono- and di-vinyl ethers of mono-, di-, tri-, tetra-ethylene or propylene glycols, trivinyl ether trimethylolpropane and divinylether of dimethanolcyclohexane, N-vinylpyrrolidone, 2-propenylether or propylene carbonate.

67. Process according to claim 57, characterized in that a photosensitizer is added to the reaction mixture.

68. Process according to claim 67, characterized in that the photosensitizer is selected from the group consisting of anthracene, diphenyl-9,10-anthracene, perylene, phenothiazine, tetracene, xanthone, thioxanthone, isopropylthioxanthone, acetophenone, benzophenone, 1,3,5-triaryl-2-pyrazolines and derivatives which are substituted on the aromatic nuclei by alkyl, oxa- or aza-alkyl radicals.

69. Process according to claim 57, characterized in that the reaction mixture additionally contains at least one monomer or prepolymer capable of free radical polymerization and a compound capable of releasing a free radical polymerization initiator under the effect of actinic radiation or β radiation or the action of heat.

70. Process for modifying the solubility properties of a polymer having groups sensitive towards acids, characterized in that it consists in subjecting said polymer to actinic radiation or β radiation, in the presence of a compound according to claim 1.

71. Process according to claim 70, characterized in that the polymer contains ester units or arylether units derived from tertiary alcohol.

72. Process according to claim 71, characterized in that the polymer is selected from the group consisting of tertiobutyl polyacrylates, tertiobutyl or tertioamyl polyitaconates, poly(tertiobutoxycarbonyloxystyrene), poly(tertiobutoxystyrene).

73. Process according to claim 70, characterized in that it is used for the chemical amplification of photoresists.

74. Composition of cationic colouring material, characterized in that it contains a compound according to claim 1.

75. Composition of cationic colouring material according to claim 74, characterized in that the negative charge(s) of the anionic group are either fixed to the molecule of the colouring material, or they constitute the counter-ion of positive charges of the colouring material.

76. A process of using an ionic compound in a catalytic reaction, said reaction selected from the group consisting of Friedel-Crafts reactions, Diels and Alder reactions, aldolization reactions, additions of Michael, reactions of allylation, reactions of pinacolic coupling, reactions of glycosilation, reactions of cyclic openings of oxetane, reactions of metathesis of alkenes, polymerizations of Ziegler-Natta type, polymerizations of metathesis type by cycle opening and polymerizations of the type metathesis of acyclic dienes, said process comprising adding the ionic compound of claim 1 to a reaction mixture.

77. Process according to claim 76, characterized in that the cation of the compound is selected from lithium, magnesium, copper, zinc, tin, trivalent metals, including rare earths, platinoids, and organometallic cations.

78. A process of carrying out chemical, photochemical, electrochemical, photoelectrochemical reactions, said process comprising utilizing the compound of claim 6 as a catalyst in said reaction, said compound being used above its melting point.

79. Electronically conductive material characterized in that it contains a compound according to claim 1.

80. Electronically conductive material according to claim 79, characterized in that, in the ionic compound, at least one of the substituents of the anionic aromatic heterocycle contains an alkyl chain having 6 to 20 carbon atoms.

81. Electronically conductive material according to claim 79, characterized in that the cationic part of the ionic compound is a polycation consisting of a doped conjugated polymer "p".

* * * * *

UNITED STATES PATENT AND TRADEMARK OFFICE
CERTIFICATE OF CORRECTION

PATENT NO.    : 6,171,522 B1  
DATED         : January 9, 2001  
INVENTOR(S)   : Michot et al.

It is certified that error appears in the above-identified patent and that said Letters Patent is hereby corrected as shown below:

Column 40,  
Line 24, please add -- optionally --.

Column 41,  
Lines 1 through 10, replace diagram with:

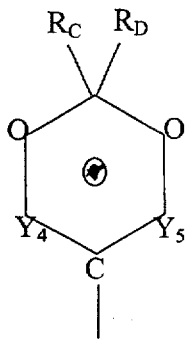

Signed and Sealed this

Fifth Day of March, 2002

*Attest:*

*Attesting Officer*

JAMES E. ROGAN  
*Director of the United States Patent and Trademark Office*